US011657899B2

(12) United States Patent
Esteves-Veríssimo et al.

(10) Patent No.: US 11,657,899 B2
(45) Date of Patent: May 23, 2023

(54) COMPUTING DEVICE

(71) Applicant: Université du Luxembourg, Grand Duchy of Luxembourg (LU)

(72) Inventors: Paulo Esteves-Veríssimo, Grand Duchy of Luxembourg (LU); Marcus Völp, Grand Duchy of Luxembourg (LU); Jérémie Decouchant, Grand Duchy of Luxembourg (LU); Maria Fernandes, Grand Duchy of Luxembourg (LU)

(73) Assignee: Université du Luxembourg, Esch/Belval (LU)

( * ) Notice: Subject to any disclaimer, the term of this patent is extended or adjusted under 35 U.S.C. 154(b) by 481 days.

(21) Appl. No.: 16/650,436

(22) PCT Filed: Sep. 26, 2018

(86) PCT No.: PCT/EP2018/076134
§ 371 (c)(1),
(2) Date: Mar. 25, 2020

(87) PCT Pub. No.: WO2019/063617
PCT Pub. Date: Apr. 4, 2019

(65) Prior Publication Data
US 2020/0234794 A1  Jul. 23, 2020

(30) Foreign Application Priority Data
Sep. 26, 2017  (LU) .................... LU100449

(51) Int. Cl.
*G16B 30/10* (2019.01)
*G16H 10/40* (2018.01)
(Continued)

(52) U.S. Cl.
CPC ........... *G16B 30/10* (2019.02); *G06F 21/602* (2013.01); *G06F 21/6245* (2013.01);
(Continued)

(58) Field of Classification Search
None
See application file for complete search history.

(56) References Cited

U.S. PATENT DOCUMENTS

2003/0039362 A1  2/2003  Califano et al.
2003/0055824 A1  3/2003  Califano
(Continued)

FOREIGN PATENT DOCUMENTS

KR    20150075468 A    7/2015
WO    2005088503 A1    9/2005
(Continued)

OTHER PUBLICATIONS

Peter J. A. Cock, Christopher J. Fields, Naohisa Goto, Michael L. Heuer, Peter M. Rice, The Sanger FASTQ file format for sequences with quality scores, and the Solexa/Illumina FASTQ variants, Nucleic Acids Research, vol. 38, Issue 6, Apr. 1, 2010, pp. 1767-1771 (Year: 2010).*

(Continued)

*Primary Examiner* — Kristine L Kincaid
*Assistant Examiner* — Felicia Farrow
(74) *Attorney, Agent, or Firm* — Dickinson Wright PLLC; Nicholas P. Coleman

(57) ABSTRACT

Genomics information such as DNA, RNA and proteins carry a wealth of sensitive information, the exposure of which risks compromising the privacy and/or business interest of individuals and companies. An apparatus, a system and methods are disclosed for protecting sensitive genomic information either as it is produced by a sequencing machine or immediately therafter, then throughout the whole genomic workflow. Raw genomic data ("reads") is detected and classified according to sensitivity. Reads are decomposed by excising the number and type of detected sensitive base or base pairs in less sensitive or insensitive parts of the (Continued)

Figure 1:
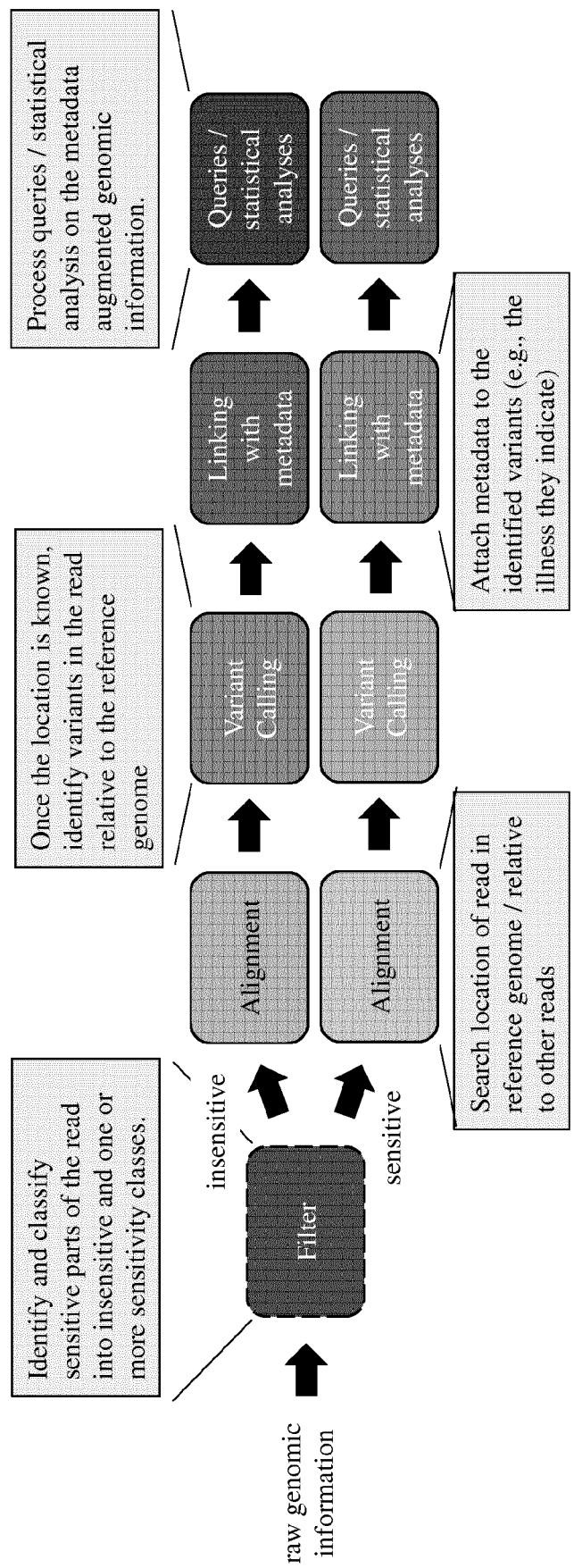

read. The genomic workflow processes the excised information locally or in a distributed fashion, preferably within trusted execution environments for increased security.

20 Claims, 9 Drawing Sheets

(51) Int. Cl.
    *G16B 50/30*      (2019.01)
    *G16B 20/50*      (2019.01)
    *G16B 50/40*      (2019.01)
    *G06F 21/60*      (2013.01)
    *G06F 21/62*      (2013.01)
    *H04L 9/08*       (2006.01)

(52) U.S. Cl.
    CPC ............ *G16B 20/50* (2019.02); *G16B 50/30* (2019.02); *G16B 50/40* (2019.02); *G16H 10/40* (2018.01); *H04L 9/0833* (2013.01)

(56) References Cited

U.S. PATENT DOCUMENTS

| | | | |
|---|---|---|---|
| 2013/0096943 | A1 | 4/2013 | Carey et al. |
| 2014/0325587 | A1 | 10/2014 | Nilsson et al. |
| 2016/0085916 | A1 | 3/2016 | Smith |
| 2017/0005787 | A1* | 1/2017 | Weaver ................ G16B 50/40 |
| 2017/0068776 | A1* | 3/2017 | Godinez-Moreno .. G16B 30/00 |
| 2018/0330054 | A1* | 11/2018 | Omari ................... G16B 30/00 |

FOREIGN PATENT DOCUMENTS

| | | | |
|---|---|---|---|
| WO | 2005088504 A1 | 9/2005 | |
| WO | WO-2013059368 A1 * | 4/2013 | ............ G06F 21/10 |
| WO | 2013067542 A1 | 5/2013 | |
| WO | 2015080987 A1 | 6/2015 | |
| WO | 2015166389 A1 | 11/2015 | |
| WO | 2016130557 A1 | 8/2016 | |
| WO | WO-2016154254 A1 * | 9/2016 | ......... G06F 21/6245 |

OTHER PUBLICATIONS

Namiki, Y., Ishida, T. & Akiyama, Y. Acceleration of sequence clustering using longest common subsequence filtering. BMC Bioinformatics 14 (Suppl 8), S7 (2013) (Year: 2013).*

International Search Report for PCT/EP2018/076134 dated Dec. 12, 2018.

Cogo, Vinicius V., et al., "A High-Throughput Method to Detect Privacy-Sensitive Human Genomic Data ", Proceedings of the 14th ACM Workshop on Privacy in the Electronic Society, WPES 15, Oct. 12, 2015, pp. 101-110.

Ayday, Erman, et al., "Privacy-Preserving Processing of Raw Genomic Data", Jul. 21, 2013 Retrieved from the Internet:—URL:http://infoscience.epfl.ch/record/187573/files/DPM_13_tech_report.pdf.

Chase, Melissa, et al., "Substring-Searchable Symmetric Encryption", International Association for Cryptologic Research, vol. 20150618:215241, Jun. 18, 2015, pp. 1-28.

Stephen F Altschul, Warren Gish, Webb Miller, Eugene W Myers, and David J Lipman. Basic local alignment search tool. Journal of molecular biology, 215(3):403-410 1990.

Mikhail J Atallah, Florian Kerschbaum, and Wenliang Du. Secure and private sequence comparisons. In Proceedings of the 2003 ACM workshop on Privacy in the elctronic society, pp. 39-44 ACM, 2003.

Mikhail J Atallah and Jiagtao Li. Secure outsourcing of sequence comparisons. International Journal of Information Security, 4(4):227-287, 2005.

Joshua Baron, Karim El Defrawy, Kirill Minkovich, Rafail Ostrovsky, and Eric Tressler. 5pm: Secure pattern matching. In Security and Cryptography for Networks, pp. 222-240. Spring 2012.

Yangyi Chen, Bo Peng, XiaoFeng Wang, and Haixu Tang. Large-scale privacy-preserving mapping of human genomic sequences on hybrid clouds. In NDSS, 2012.

Emiliano De Cristofaro, Sky Faber, and Gene Tsudik. Secure genomic testing with size- and position-hiding private substring matching. In Proc of the 12th ACM Workshop on Privacy in the Electronic Society, pp. 107-118, 2013.

Stephanie OM Dyke, Edward S Dove, and Bartha M Knoppers. Sharing health-related data: a privacy test? NPJ genomic medicine, 1(1):16024-1, 2016.

Michael Gross. Trusted booting as the foundation of authentic base systems. In reliable information systems—computer science reports No. 271, pp. 190-207, Darmstadt, 1991. GI conference1991.

Yan Huang, David Evans, Jonathan Katz, and Lior Malka. Faster secure two-party computation using garbled circuits. In USENIX Security Symposium, vol. 201, 2011.

Somesh Jha, Louis Kruger, and Vitaly Shmatikov. Towards practical privacy for genomic computation. In Security and Privacy, 2008. SP 2008. IEEE Symposium on, pp. 216-230. IEEE, 2008.

CHeng Li and Richard Durbin. Fast and accurate short read alignment with burrows-wheeler transform. Bioinformatics, 25(14):1754-1760, 2009.

Ben Langmead, Cole Trapnell, Mihai Pop, Steven L Salzberg, et al. Ultrafast and memory-efficient alignment of short dna sequences to the human genome. Genome biol, 10(3):R25, 2009.

Victoria Popic and Serafim Batzoglou. Privacy-preserving read mapping using locality sensitive hashing and secure kmer voting. bioRxiv, 2016.

Victoria Popic and Serafim Batzoglou. A hybrid cloud read aligner based on minhash and kmer voting that preserves privacy. Nature communications, 8:15311, 2017.

N. Sadat, M. Aziz, N. Mohammed, F. Chen, S. Wang, and X. Jiang. Safety: Secure gwas in federated environment through a hybrid solution with intel sgx and homomorphic encryption. https://arxiv.org/pdf/1703.02577.pdf, Mar. 2017.

Kehuan Zhang, Xiaoyong Zhou, Yangyi Chen, XiaoFeng Wang, and Yaoping Ruan. Sedic: privacy-aware data intensive computing on hybrid clouds. In Proc. of the 18th ACM Conf. on Computer and Comm. Security, pp. 515-526, 2011.

* cited by examiner

Figure 1 [prior art]

privacy threshold prevents
immediate disclosure

COMPUTING DEVICE

This application is the national stage of international patent application no. PCT/EP2018/076134 filed on Sep. 26, 2018, which in turn claims priority from Luxembourg Patent Application No. LU100449 filed on Sep. 26, 2017, the disclosures of which are incorporated herein by reference in their entirety.

TECHNICAL FIELD

The present invention relates to an improved computing device, system and method. More particularly, though not exclusively, the present invention relates to a genomic information device, system and method or process for processing genomic information.

BACKGROUND

Genomic information such as DNA, RNA and proteins carry a wealth of sensitive information, the exposure of which risks compromising the privacy and/or business interests of individuals and companies Genomic information is produced by sequencing machines from biological samples, typically as raw genomic data in the form of unfiltered sequences of contiguous bases or base pairs, which are called reads in the art, and so which encode the sensitive information inherent to each sample.

Examples of sensitive information include disease-related genes, ethnographic grouping and other distinguishing physical attributes, the exposure of which can indicate the susceptibility of an individual to certain types of illnesses, allow re-identification of the individual and/or reveal business secrets about genetic modifications.

Many techniques have been developed, and then improved, either to optimise genomic information processing or to mitigate the potential for disclosing and/or disseminating sensitive information contained therein. Herein the Inventors will make reference to the following prior art disclosures:

[AGM+90] Stephen F Altschul, Warren Gish, Webb Miller, Eugene W Myers, and David J Lipman. Basic local alignment search tool. *Journal of molecular biology*, 215(3):403-410, 1990.

[AKD03] Mikhail J Atallah, Florian Kerschbaum, and Wenliang Du. Secure and private sequence comparisons. In *Proceedings of the 2003 ACM workshop on Privacy in the electronic society*, pages 39-44. ACM, 2003.

[AL05] Mikhail J Atallah and Jiangtao Li. Secure outsourcing of sequence comparisons. *International Journal of Information Security*, 4(4):277-287, 2005.

[ARH+14] Erman Ayday, Jean Louis Raisaro, Urs Hengartner, Adam Molyneaux, and Jean-Pierre Hubaux. Privacy-preserving processing of raw genomic data. In *Data Privacy Management and Autonomous Spontaneous Security*, pages 133-147. Springer, 2014.

[BEDM+12] Joshua Baron, Karim El Defrawy, Kirill Minkovich, Rafail Ostrovsky, and Eric Tressler. 5 pm: Secure pattern matching. In *Security and Cryptography for Networks*, pages 222-240. Springer, 2012.

[CBCV15] Vinicius V Cogo, Alysson Bessani, Francisco M Couto, and Paulo Verissimo. A high-throughput method to detect privacy-sensitive human genomic data. In *14th ACM Workshop on Privacy in the Electronic Society*, pages 101-110. ACM, 2015.

[CPWT12] Yangyi Chen, Bo Peng, XiaoFeng Wang, and Haixu Tang. Large-scale privacy-preserving mapping of human genomic sequences on hybrid clouds. In *NDSS*, 2012.

[DCFT13] Emiliano De Cristofaro, Sky Faber, and Gene Tsudik. Secure genomic testing with size- and position-hiding private substring matching. In *Proc. of the 12th ACM Workshop on Privacy in the Electronic Society*, pages 107-118, 2013.

[DDK16] Stephanie O M Dyke, Edward S Dove, and Bartha M Knoppers. Sharing health-related data: a privacy test? *NPJ genomic medicine*, 1(1):16024-1, 2016.

[Gro91] Michael Gross. Vertrauenswürdiges booten als grundlage authentischer basissysteme. In *Verlässliche Informationssysteme—Informatik-Fachberichte Nr. 271*, pages 190-207, Darmstadt, 1991. GI-Fachtagung VIS '91.

[HEKM11] Yan Huang, David Evans, Jonathan Katz, and Lior Malka. Faster secure two-party computation using garbled circuits. In *USENIX Security Symposium*, volume 201, 2011.

[JKS08] Somesh Jha, Louis Kruger, and Vitaly Shmatikov. Towards practical privacy for genomic computation. In *Security and Privacy, 2008. SP 2008. IEEE Symposium on*, pages 216-230. IEEE, 2008.

[LD09] Heng Li and Richard Durbin. Fast and accurate short read alignment with burrows-wheeler transform. *Bioinformatics*, 25(14):1754-1760, 2009.

[LTP+09] Ben Langmead, Cole Trapnell, Mihai Pop, Steven L Salzberg, et al. Ultrafast and memory-efficient alignment of short dna sequences to the human genome. *Genome biol*, 10(3):R25, 2009.

[pata] End to end trusted communications infrastructure. Patent US20160142396.

[patb] Secure biometric data capture, processing and management. Patent WO21620052A1.

[patc] Secure booting of an electronic apparatus with smp architecture. U.S. Pat. No. 7,624,261.

[patd] Systems and methods for protecting governing genomic and other information. Patent CA2852916A1.

[pate] Trust establishment between a trusted execution environment and peripheral devices. Patent US20160182499.

[PB16] Victoria Popic and Serafim Batzoglou. Privacy-preserving read mapping using locality sensitive hashing and secure kmer voting. *bioRxiv*, 2016.

[PB17] Victoria Popic and Serafim Batzoglou. A hybrid cloud read aligner based on minhash and kmer voting that preserves privacy. *Nature communications*, 8:15311, 2017.

[SAM+17] N. Sadat, M. Aziz, N. Mohammed, F. Chen, S. Wang, and X. Jiang. Safety: Secure gwas in federated environment through a hybrid solution with intel sgx and homomorphic encryption. https://arxiv.org/pdf/1703.02577.pdf, March 2017.

[She16] Robert Shelton. System, method and apparatus to enhance privacy and enable broad sharing of bioinformatic data. Patent WO2016154254, March 2016.

[Smi14] Ned M. Smith. Privacy preserving genome sequence management. Patent US2016085916, September 2014.

[WH05] Mitch Webster and Oliver Horlacher. Secure transaction of dna data. Patent WO2005088504, March 2005.

[WO215] Genomic informatics service. Patent WO2015166389, April 2015.

[ZZC+11] Kehuan Zhang, Xiaoyong Zhou, Yangyi Chen, XiaoFeng Wang, and Yaoping Ruan. Sedic: privacy-aware data intensive computing on hybrid clouds. In *Proc. of the* 18*th ACM Conf. on Computer and Comm. Security*, pages 515-526, 2011.

| | |
|---|---|
| US2013096943 | Intertrust Technologies Corporation |
| US2017005787 | Genformatic LLC |
| WO2016154254 | Private Access Inc |
| US2016085916 | Intel Corp |
| KR20150075468 | KT Corp |
| WO2016130557 | Bigdatabio LLC |
| WO2015166389 | Intertrust Technologies Corp |
| US2015317490 | Intertrust Technologies Corp |
| WO2015080987 | Microsoft Corp |
| US2014325587 | Intertrust Technologies Corp |
| WO2013067542 | Genformatic LLC |
| WO2005088504 | Carsha Co Ltd |
| WO2005088503 | Carsha Co Ltd |
| US20003039362 | First Genetic Trust Inc |
| US2003055824 | First Genetic Trust Inc |

Notwithstanding the consequent body of prior art teachings in the field, disadvantages continue to beset genomic data processing techniques for facilitating genomic research, in particular as regards the security of processing that genomic information and/or the control of sequenced genomic data transfer. An object of the invention is therefore to obviate, or at least mitigate, at least one such disadvantage.

SUMMARY

The present invention provides a methodology, and both a device and a distributed system implementing this methodology for protecting sensitive genomic information, either immediately after its production by a sequencing machine or in parallel with the sequencing taking place depending on the embodiment, and thereafter throughout whole genomic workflows. Improving upon published state-of-the-art filtering methods for detecting and classifying raw genomic data, the principles of the present invention are to decompose reads by excising the number and type of bases or base pairs corresponding to sensitive genomic information in less sensitive parts of a read, and to adjust the genomic workflow for processing the excised information securely, in a local or distributed manner subject to the embodiment. In some particularly useful embodiments, the inventors rely upon trusted execution environments (TEEs) and introduce the concept of sealed intermediate-result extraction for allowing TEEs to cooperate securely when they process sensitive genomic information in a local or distributed context.

According to a first aspect of the present invention, there is therefore provided a computing device comprising at least one data collection arrangement comprising at least one sensor for reading genomic information into at least one read of any length, the or each read comprising a sequence of bases; at least one data processing arrangement adapted to filter each read for detecting one or more sensitive bases in the sequence, and to excise each detected sensitive base from the or each filtered read for outputting an insensitive sequence; and at least one data storage arrangement adapted to store said read genomic information.

In an embodiment of the device, the data processing arrangement may be further adapted to detect the or each sensitive bases by comparing the sequence with a number and type of predetermined base (s).

In an embodiment of the device, the or each data collection arrangement, the or each processing arrangement, and the or each storage arrangement may be provided either locally to one another, optionally within a single or common enclosure or on a common substrate or board; or may be provided separate or remotely from one another and/or are connected through or via a local area network.

In an embodiment of the device, one or more of the arrangements of the device may implement a trusted execution environment for processing genomic information. In a variant of this embodiment, the at least one sensor may be adapted to provide a secure communication channel to the trusted execution environment.

An embodiment of the device may be adapted to read the genomic information into a long read of at least 1,000 bases.

Any of the above embodiments of the device may usefully be implemented within a genomic information sequencing machine.

According to a second aspect of the present invention, there is also provided a system, such as a genomic information sequencing system, comprising data collection means comprising at least one sensor for reading genomic information into at least one read of any length, the or each read comprising a sequence of bases; data processing arrangement adapted to filter each read for detecting one or more sensitive bases in the sequence, and to excise each detected sensitive base from the or each filtered read for outputting an insensitive sequence; and data storage means adapted to store said read genomic information.

In a distributed embodiment of the system, the data collection means, the data processing means and the data storage means may comprise a plurality of computing devices that are provided remotely from one another and respectively connected to a network.

According to a third aspect of the present invention, there is also provided a method of processing genomic information comprising the steps of reading genomic information from at least one data collection arrangement comprising at least one sensor, into at least one read of any length, the or each read comprising a sequence of bases; executing a filtering process on each read with at least one data processing arrangement for detecting one or more sensitive bases in the sequence; executing an excising process on each filtered read with the at least one data processing arrangement for excising each detected sensitive base therefrom and outputting an insensitive sequence; and storing said read genomic information in at least one data storage arrangement.

In an embodiment of the method, the or each read may comprise at least 30 bases.

An embodiment of the method may comprise the further step of splitting the or each sequence into multiple data sets, wherein at least one data set contains each insensitive base, and at least one data sets contains each detected sensitive base and a reference to the location in the sequence of each excised base.

In an embodiment of the method, the step of executing the excising process may split the sequence into an insensitive level and at least one sensitive level.

In a variant of either of these previous embodiments of the method, the step of executing the excising process may further comprise replacing one or more detected sensitive base(s) with a character "N", apt to represent any nucleotide according to the FASTA and FASTQ file format. In a further variant, the step of executing the excising process may further comprise replacing one or more detected sensitive base(s) with a character "@", apt to indicate the location in the sequence at which the or each detected sensitive base is excised.

An embodiment of the method may comprise the further step of aligning the or each read and wherein the step of excising is performed either before or after aligning as a function of the read length. In a variant of this embodiment, the step of aligning may further comprise aligning the or each excised reads to at least one reference genome or to other reads. A variant of this further embodiment, may comprise the further steps of comparing the or each aligned read against the or each reference genome or said other reads for detecting one or more differences; and storing detected difference(s) and their respective location(s) into one or more data structures. In a variant of this latest embodiment, the step of comparing may be further for detecting any bases that is both adjacent to any detected sensitive base in the aligned read and has a lower sensitivity relative thereto, according to whether the adjacent base is apt to indicate said detected sensitive base in the aligned read; and the step of executing an excising process is preferably performed upon each detected adjacent base.

An embodiment of the method may comprise the further step of instantiating at least one trusted execution environment (TEE) with a respective level of access to sensitive date sets containing detected sensitive base(s); wherein the step of comparing the or each aligned read is performed within the instantiated TEE.

An alternative embodiment of the method may comprise the further steps of instantiating at least one trusted execution environment (TEE) with a respective level of access to sensitive date sets containing detected sensitive base (s); receiving at least one data query for genomic information including at least one sensitive data set; classifying each query according to a comparison of the sensitivity of each sensitive data set against the access level of the TEE; processing the query whenever the access level of the TEE is equal to or exceeds the data set sensitivity; and outputting queried genomic information.

In a variant of this embodiment, the method may comprise the further step of decomposing the or each received query into a plurality of subqueries; wherein the step of instantiating may further comprise instantiating at least one aggregating trusted execution environment (TEE); the step of classifying may further comprise classifying each subquery; and the step of processing may further comprise processing each subquery and aggregating genomic information output from processed subqueries with the aggregating TEE.

In a variant of either of these previous embodiments of the method, the step of outputting queried genomic information may further comprise executing the filtering and excising processes on the queried genomic information.

In a further variant of these previous embodiments, the step of instantiating may further comprise negotiating at least one secure channel between at least two TEEs, the method comprising the further step of either encrypting genomic information data at a data-sending TEE, wherein only a data-receiving TEE may decrypt it; or encrypting genomic information data with a key shared by all TEEs of a same access level.

Any of the embodiments of the method disclosed herein may usefully be implemented by a genomic information sequencing machine or system.

According to a fourth aspect of the present invention, there is also provided a networked system comprising network-connected data processing means adapted to perform data processing steps of the method of the third aspect of the present invention.

According to a fifth aspect of the present invention, there is also provided a computer readable medium for storing computer readable instructions which, when executed by at least one data processing device, cause the or each data processing device to read genomic information from at least one sensor, into at least one read of any length, the or each read comprising a sequence of bases; execute a filtering process on each read for detecting one or more sensitive bases in the sequence; execute an excising process on each filtered read for outputting an insensitive sequence which omits each detected sensitive base; and store the genomic information read in at least one data storage arrangement.

For any of the embodiments disclosed herein, a reference to a base may comprise a reference to a base pair instead.

Other aspects are as set out in the claims herein.

BRIEF DESCRIPTION OF THE DRAWING FIGURES

Figure 2:
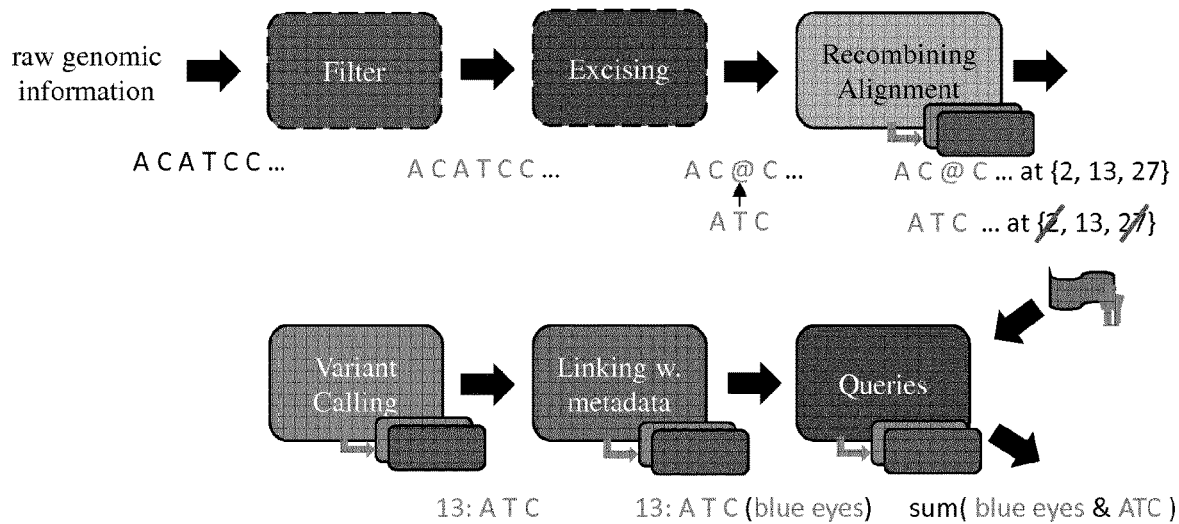
Figure 3:
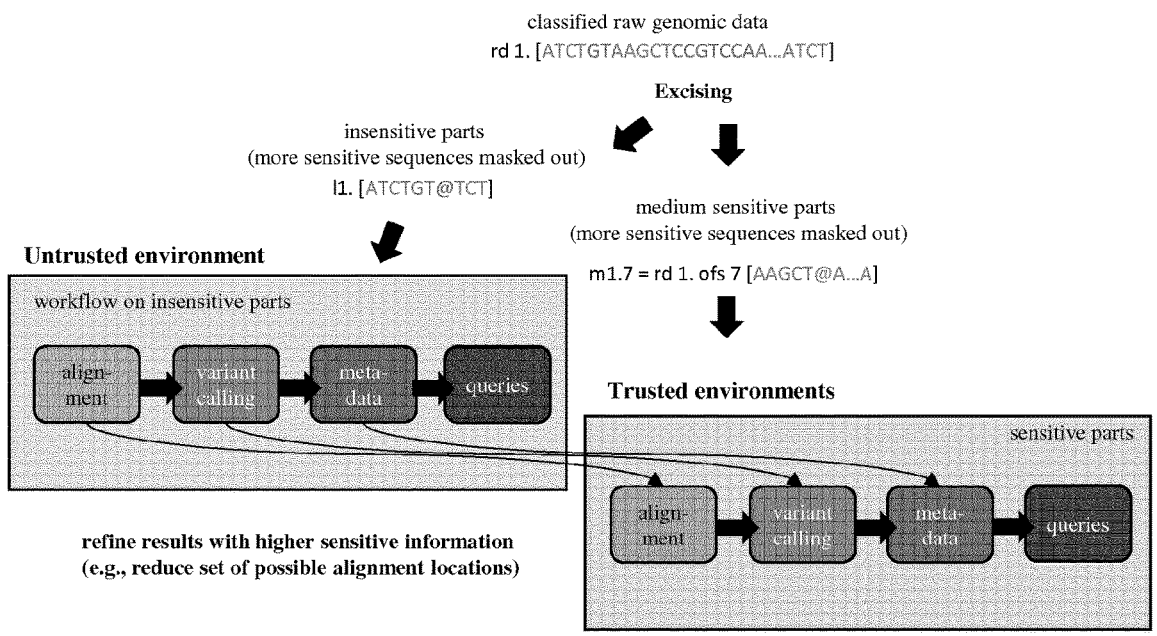
Figure 4:
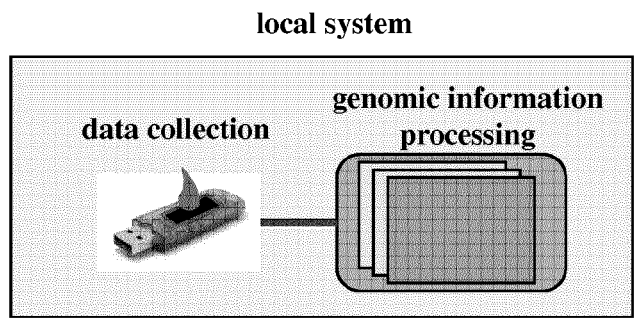
Figure 5:
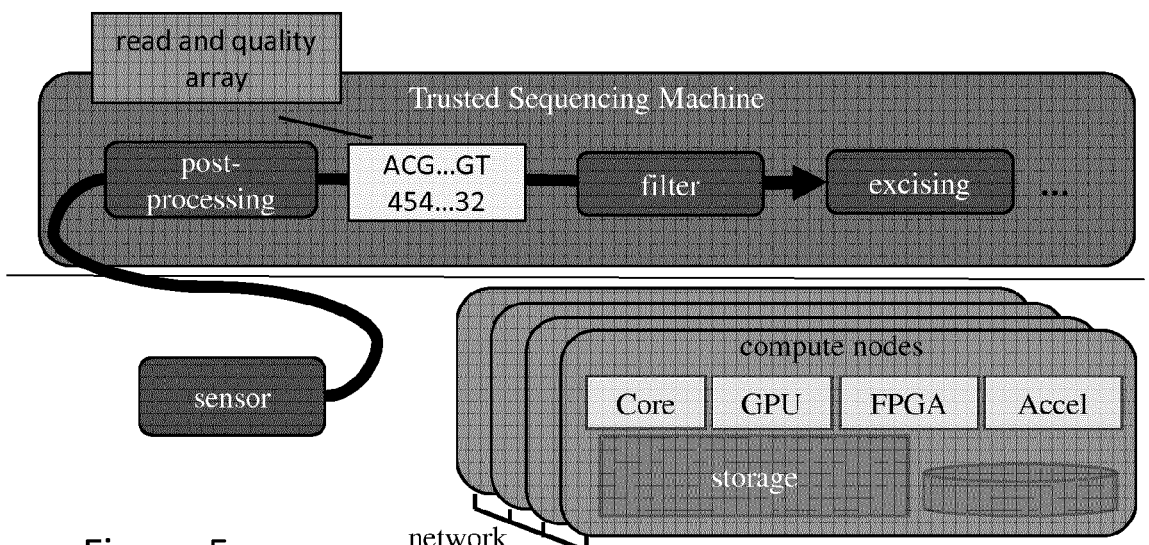
Figure 6:
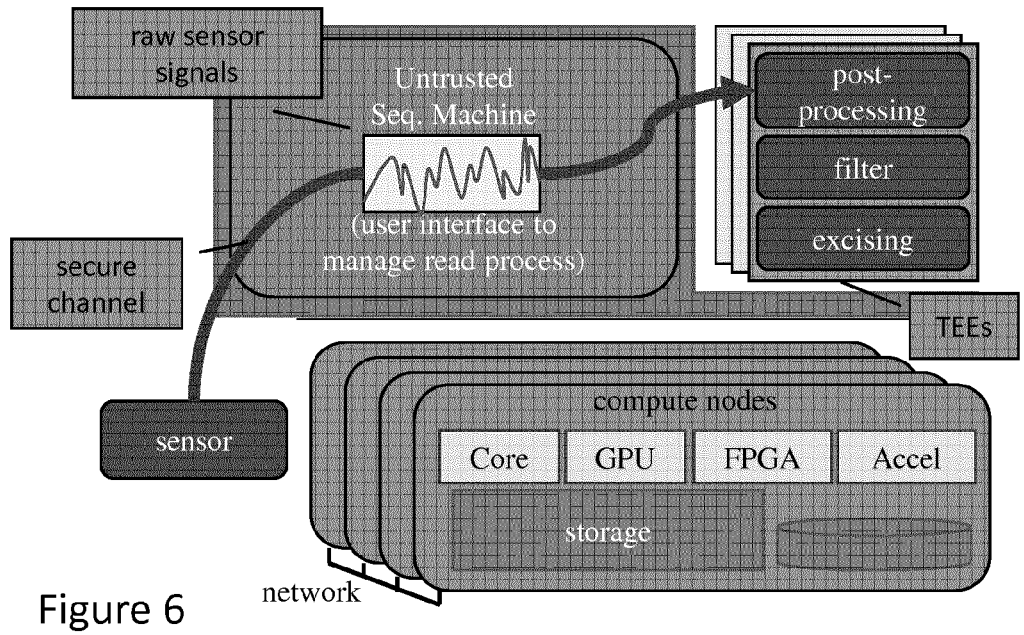
Figure 7:
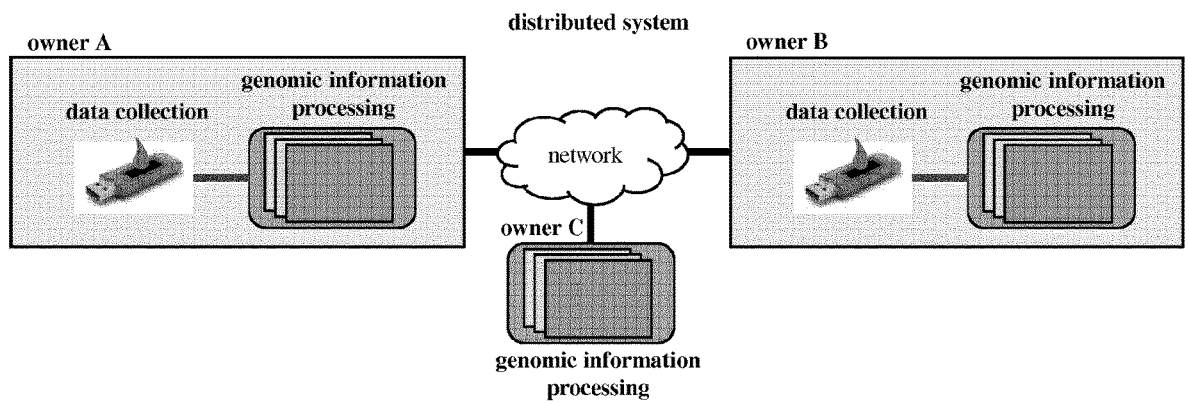
Figure 8:
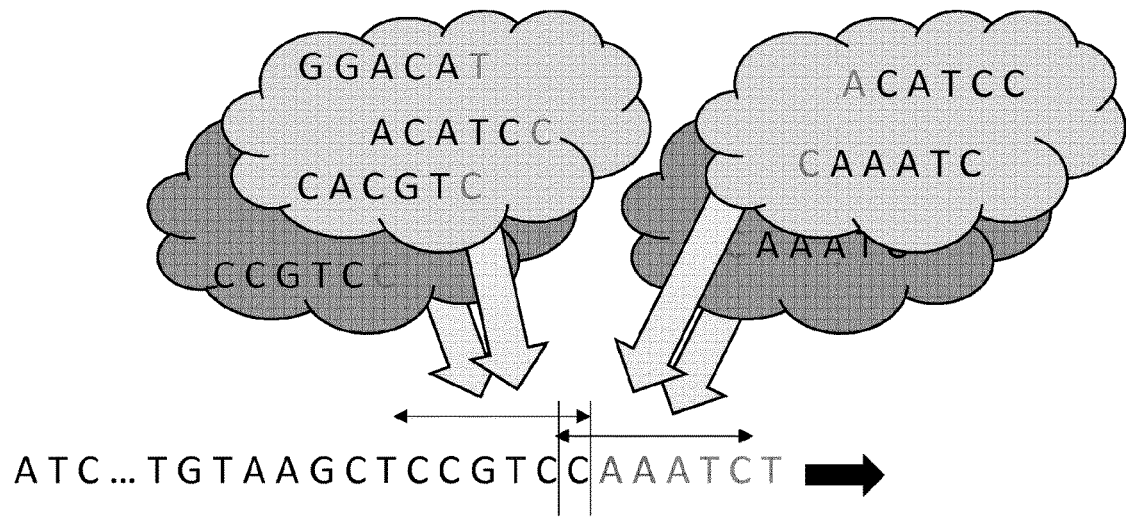
Figure 9:
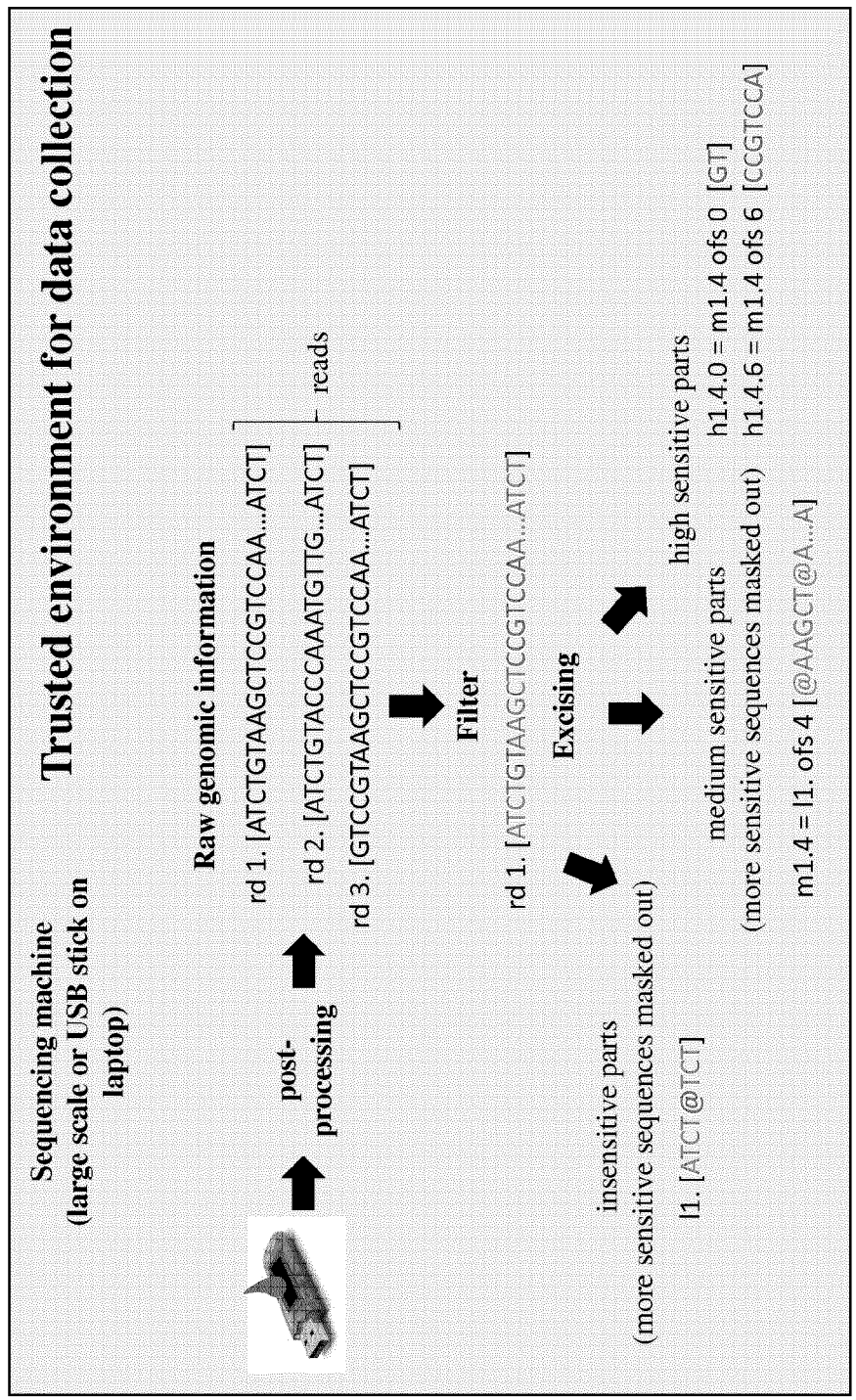
Figure 10:
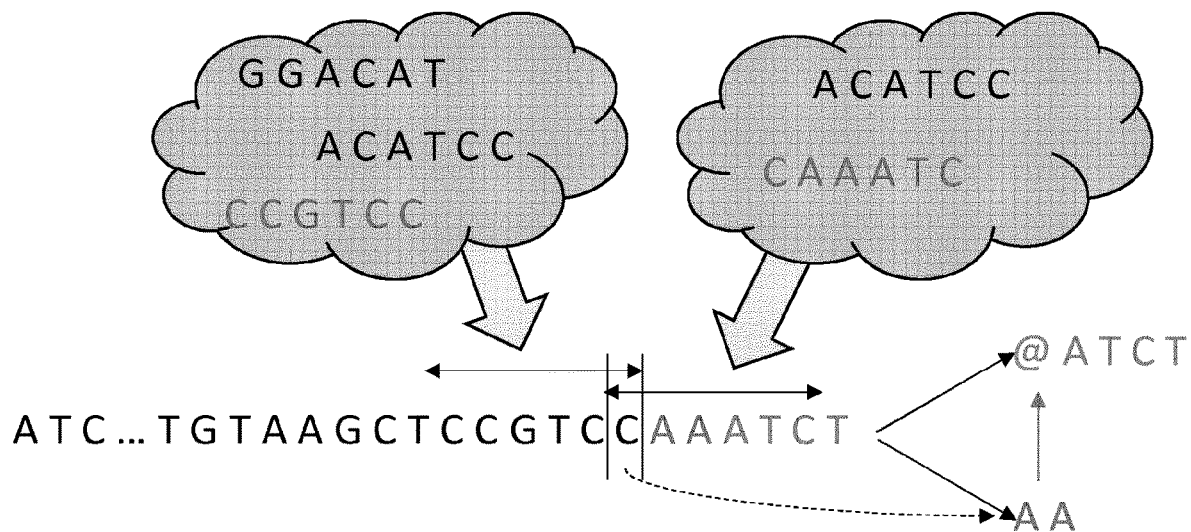
Figure 11:
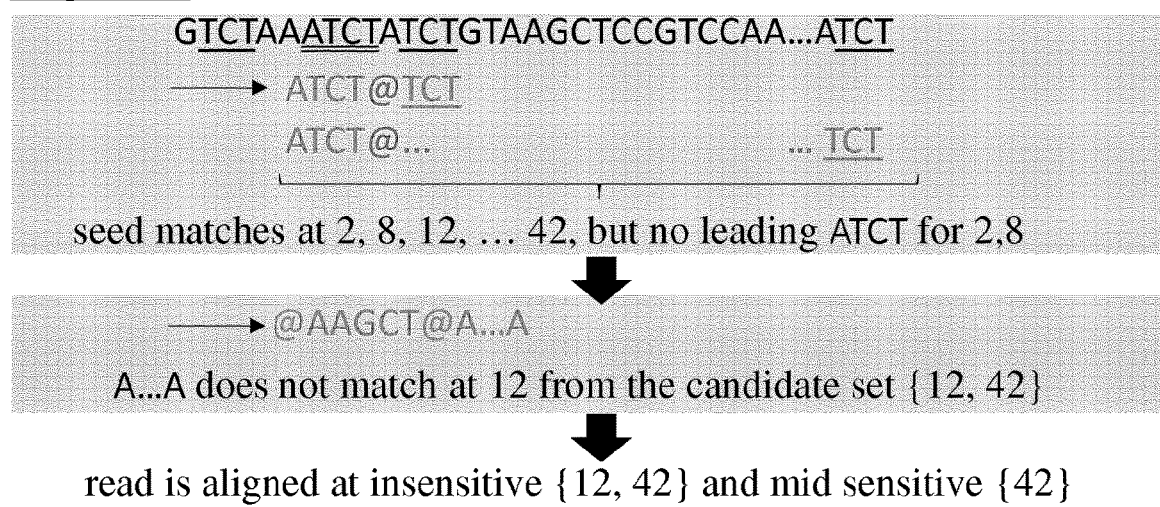
Figure 12:
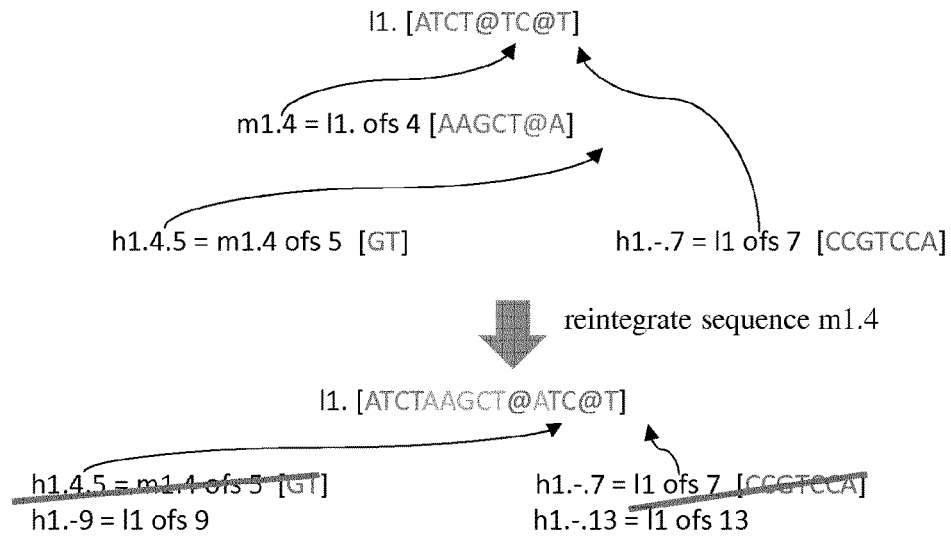
Figure 13:
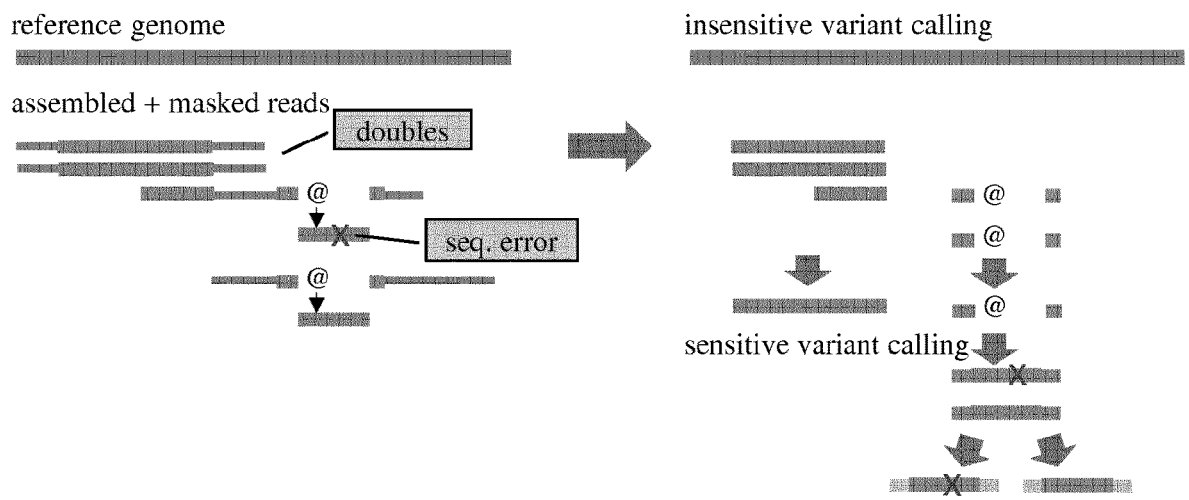
Figure 14:
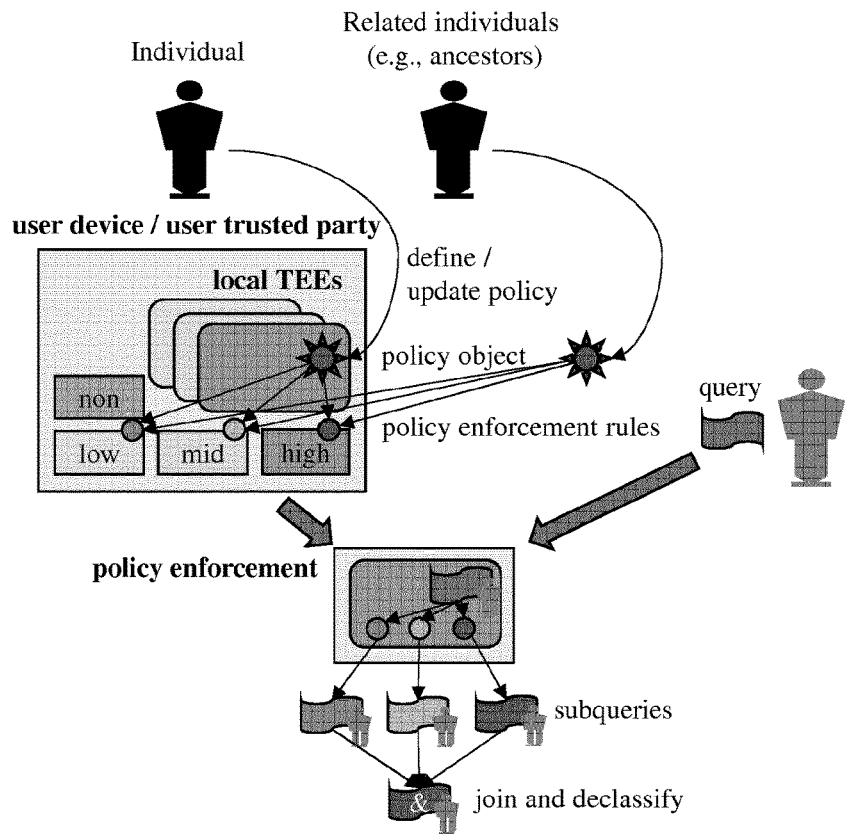
Figure 15:
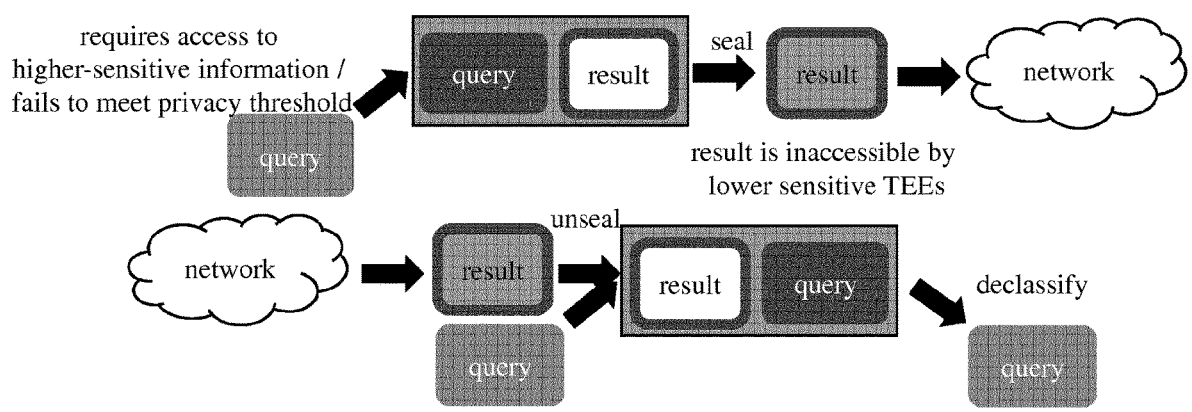
Figure 16:
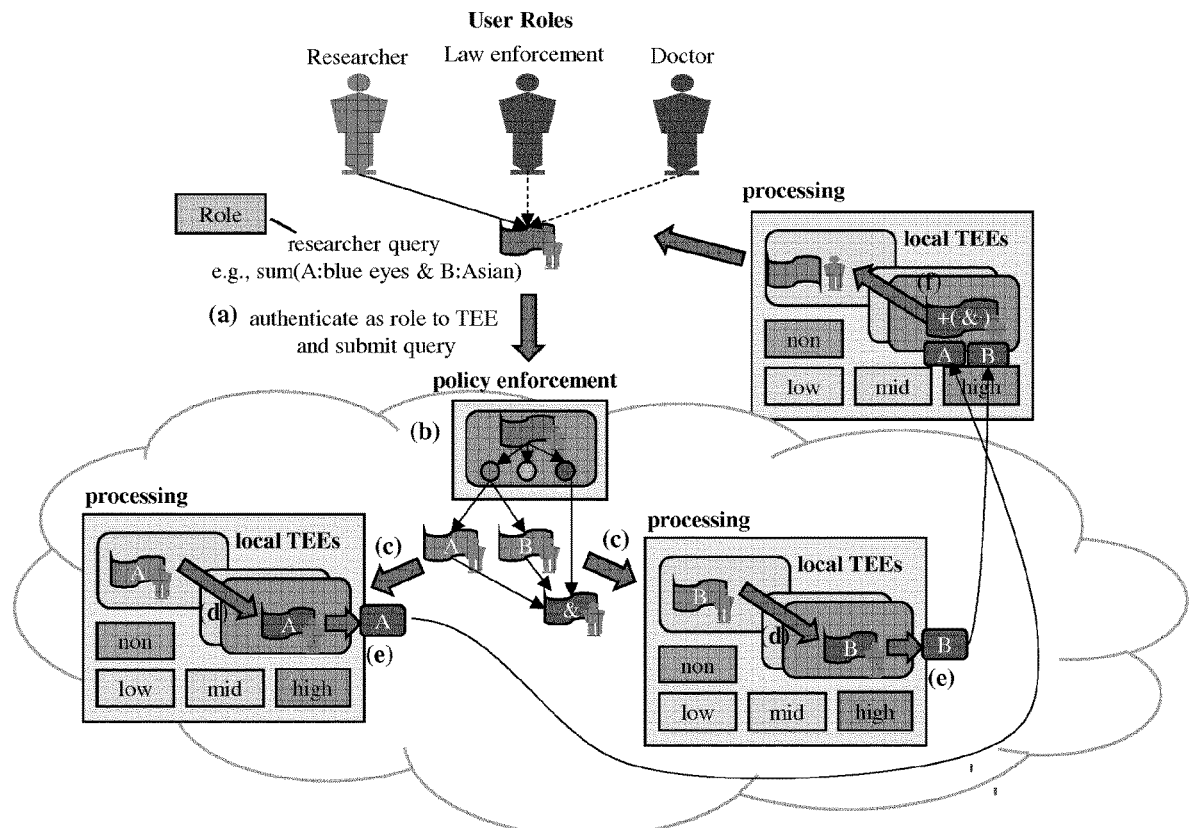
Figure 17:
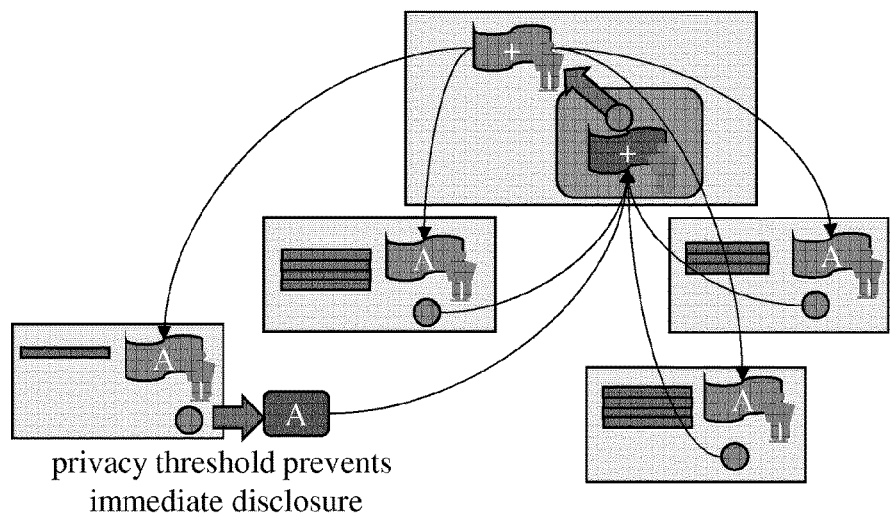

Embodiments of the present invention will now be described by way of example only, and with reference to accompanying drawings, which are:

FIG. 1 a genomic information process according to the prior art;

FIG. 2 a genomic information process according to an embodiment of the present invention;

FIG. 3 a further genomic information process according to an embodiment of the present invention;

FIG. 4 a genomic information processing apparatus according to an embodiment of the present invention;

FIG. 5 a genomic information processing apparatus according to an embodiment of the present invention;

FIG. 6 a genomic information processing apparatus according to an embodiment of the present invention;

FIG. 7 a distributed genomic information processing system according to an embodiment of the present invention;

FIG. 8 a genomic information filtering processing according to an embodiment of the present invention;

FIG. 9 a genomic information excising process according to an embodiment of the present invention;

FIG. 10 an integrated genomic information filtering and excising step according to an embodiment of the present invention;

FIG. 11 a genomic information recombining process according to an embodiment of the present invention;

FIG. 12 a genomic information reintegration process, according to an embodiment of the present invention;

FIG. 13 a genomic information variant calling process according to an embodiment of the present invention;

FIG. 14 an excised genomic information controlled access process according to an embodiment of the present invention;

FIG. 15 a genomic information sealing process according to an embodiment of the present invention;

FIG. 16 a genomic information distributed query process according to an embodiment of the present invention; and FIG. 17 a further genomic information distributed query process according to an embodiment of the present invention.

DETAILED DESCRIPTION

There will now be described by way of example specific modes of implementation contemplated by the inventors. In the following description numerous specific details are set forth in order to provide a thorough understanding. It will however be clear to the skilled reader, that the present invention may be practiced without limitation to these specific details. Moreover, well-known methods and structures have not been described in detail so as not to unnecessarily obscure the description. Nevertheless, certain definitions are provided initially, in order to facilitate the skilled reader's understanding of the inventors' terminology in the description hereunder.

"Sensitivity level" means a categorisation of a base, a base pair and/or a read, and groups thereof, according to one or more of its rarity, the criticality of the information which it reveals about an individual, the type and extent of privacy attacks which it enables or attracts, and similar properties and attributes closely correlated with, typically, the health and identity profile of an individual.

"Long read" means a sequence of nucleotides, or bases, with a length exceeding 30 nucleotides, optionally along with a vector of base quality scores. "Short read" means a sequence of 30 nucleotides, or bases. Both short and long reads typically include both sensitive nucleotides, i.e. those which represent a security risk if and when identified in a sequence, and insensitive nucleotides, i.e. those which correspond to a generic property. On the basis of this definition, a classification methodology filtering whole reads only, would lead to the classification of the vast majority of reads as sensitive.

"Long read filtering" means a method of identifying nucleotides and/or sub-sequences thereof and their sensitivity level inside long reads.

"Excising", in the context of excising sensitive information, means a method of partitioning sub-sequences of a long read according to a set of one or more sensitivity levels, into sensitivity level-respective data set(s) that may be kept apart for later processing steps. For a given sensitivity level, excising effectively removes any base(s) and sub-sequence(s) of any length and type, that are classified as more sensitive than the sequence under consideration; wherein sub-sequences of a higher sensitivity level may be kept with a reference to their original location in the lower-sensitivity excised sequence.

"Read alignment" means the process of locating the origin of a read in a genome, by identifying matching locations in one or more reference genomes, or in other reads. "De novo assembly" means the process of reconstructing a genome, by identifying matching overlaps between reads. The skilled reader will appreciate from the foregoing, that any reference to 'alignment' means read alignment and de novo assembly interchangeably.

The present invention concerns genomic information processing and addresses the whole genomics workflow, from the point in time at which genomic information is produced in so-called next-generation sequencing machines (NGS), and throughout the whole lifecycle of this data. NGS machines decipher segments of deoxyribonucleic acid (DNA) and ribonucleic acid (RNA), produce sequences of between thirty and several thousand bases (nucleotides), and provide a confidence value for each base indicative of the accuracy of the read is at the location. Following sequencing, reads need to be aligned to one or more reference genome(s) or, without such referencing data structures, to other reads from the same genome (reads assembly), for identifying their location in the genome and reconstructing the gene as a whole. Once reconstructed, statistical methods and other queries can then be applied to a genome, for example to obtain new insights in research studies, to re-identify individuals in forensic analyses, or to synthesize personalized medicine for patients.

The size of a human genome, estimated at approximately 3 Giga base pairs ("BPs") and the speed at which modern sequencing machines produce reads, with sequencing the full genome of an individual currently taking approximately one day, require increased computing power and resources. Operational costs and the exponential growth of genomic data production tend to discourage private local installations, in favour of more distributed genomic information processing infrastructures, including cloud-based in emerging instances. However, current techniques for securing genomic information and processing operations thereon, such as operations on genomic data protected cryptographically through e.g. homomorphic encryption, or proposals to execute the whole genomic workflow in trusted-execution environments ("TEEs"), are limited by the slow speed of cryptographic methods caused by the limited data processing resources available in state-of-the-art TEEs. The present invention therefore follows a different approach.

On the basis of privacy filtering methods for genomic information published by Cogo et al. [CBCV15], the inventors have developed a method for processing reads of any length, wherein sensitive base(s) in the read are excised for embedding privacy in the output genomic sequence, together with an apparatus and methods for securely processing excised genomic information in a local or distributed manner.

FIG. 1 illustrates the genomic workflow as taught by Cogo et al., which replicates the traditional genomic information workflow for each sensitivity level and with the genomic data classified at that level. The privacy filter of Cogo et al. classifies short reads of 30 BPs into two categories: sensitive reads and insensitive reads. Because it removes entire short reads with any or more bases therein that are deemed sensitive, this simplistic filter is apt to over-filter input genomic information and so to remove excess meaning from output genomic information. Moreover, the Cogo et al. approach of classifying whole reads cannot scale usefully to longer reads of 1,000 bases or more, because such a filter would end up classifying all input reads as sensitive: by way of reference, at least 90% of 1,000 base pair sequences are known to contain a sensitive substring.

The present invention extends this filter to consider multiple levels of sensitivity that allow subsequent algorithms to match performance and assurance of the implementation to the protection goals appropriate for the information's sensitivity levels. For example, fast plaintext alignment can be used to identify the location of insensitive reads, whereas more secure homomorphic encryption algorithms can be used to perform this task for higher sensitive information.

The methodology, both of the state of the art and according to the present invention, assumes classified raw genomic information: at each location in a read, wherein the read is assumed to reveal the base (or base-pair), the confidence of correctness of the read, and the sensitivity level at which this base is classified. Sensitivity layers are built according to the sensitivity of the genomic information which they contain. Privacy sensitivity can be defined qualitatively for attributes of an individual (e.g. for a variation that identifies an individual as European), or quantitatively using the frequencies of variations in a population (e.g. a rare disease-related gene would have a high sensitivity).

A state of the art genomic workflow pipeline is shown in FIG. 1, the first stage of which, filtering, classifies the raw genomic information. The filter receives post-processed sensor signals (i.e. the bases plus a quality value) by way of input, and returns the sensitivity level of the read. Herein, two types of filters are distinguished: whole-read classifiers, which decide whether a read belongs to a given sensitivity level or not on a per-read basis, and which are considered state-of-the-art and as used in the pipeline of FIG. 1; and substring classifiers, introduced by the present invention, which identify parts of a read as belonging to a given sensitivity level.

Which type of filter is prescribed, depends on the length of the read produced. Short reads contain too few significant bases to reliably identify sensitive variations. Therefore, for short reads, whole read classifiers are used and the output is the sensitivity level at which the whole read is classified. Only after alignment would it be possible to refine the classification choice and to extract and excise only those regions of a read that belong to a sensitive variation. Substring classifiers are, on the other hand, indicated for long reads, because a large percentage of long reads contain at least one sensitive part and would thus always be classified as sensitive by a whole-read classifier: it is known that over 90% of reads counting 1000 bases contain at least one genomic variation, and would therefore be considered sensitive by a whole-read classifier. A new filtering process has thus been developed, so that one match of a sensitive sequence in a filter leads to one base declared sensitive, thereby decreasing the number of bases considered sensitive from 80%, which is impractical, to 10%.

With reference to the prior art privacy filter of Cogo et al. [CBCV15] and its extension to long reads by the principles described herein, both Cogo's filter and the present filter apply Bloom filters trained with known sensitive sequences. Cogo suggested training a single Bloom filter with reads that are known to be sensitive. The present invention extends Cogo's filter to recognize sequences at different sensitivity levels, by splitting the training set by sensitivity level, and by using one Bloom filter per sensitivity level, wherein reads are then classified sensitive at a given level, if the filter for this given level detects the read.

The system of the invention applies to raw genomic information, typically before a step of alignment in traditional genomic data processing, and is fully automated. It therefore eliminates the risk of privacy attacks during the computationally-intensive alignment step, and results in an overall more secure method. The classification of sequences does not depend on the knowledge of an error-prone user, but is automatic, by reference to an updateable knowledge base. Any post processing inherits this classification, making redundant most if not all operations described in prior art references. Sensitive parts of reads are not reintegrated to perform such an annotation with user-specific policies. Instead, raw genomic data is directly classified, sensitive parts of which are excised and, later, policies remain associated to excised parts.

In the present approach, a genomic sequence is split into several sub-sequences as a function of sensitivity levels, wherein the sub-sequences are distributed in different locations, before entering the computing pipeline. Sub-sequences contain excised information that also imply modifications in the computing pipelines. Each sensitivity level contains useful data, and the present methods operate directly on the data at their individual sensitivity levels by recombining results from lower sensitivity levels with the additional information obtained from analysing the excised parts at the current sensitivity level. Separated datasets need not to be recombined prior to subsequent analyses, mitigating privacy attacks on this recombined data.

Accordingly, the invention provides a long-read substring filter to classify substrings of raw genomic information into multiple sensitivity levels, consisting of an insensitive level and at least one sensitive level. Substrings with a higher sensitivity are excised from strings with a lower sensitivity, such that observers, including potential adversaries, who are authorized only to learn about the strings with a lower sensitivity, cannot reconstruct the excised sensitive information, either from the size of the excised region(s) or from their location, after aligning the strings with a lower sensitivity. The method of the invention maintains excised bases or strings thereof apart, and embodiments securely process excised information. Rather than replicating the steps of the workflow at each level, which would exhaust the resources of trusted execution environments (TEEs), embodiments of the method incorporate partial results obtained for lower sensitivity information and which can be executed in a distributed context for matching the performance requirements of genomic information processing. Data processing embodiments of the method preferably rely upon TEEs in the data collecting subsystems, which may be either local or distributed, and ensure that sensitive genomic information never exits TEEs in unprotected form. Collaborating TEEs process sensitive partial results within their secured context, wherein the data output by such secured processing is referred herein as sealed intermediate-results.

More precisely, the method of the invention introduces the following operations on excised genomic information:

recombining long-read alignment refers to the alignment of reads with excised sequences by determining a candidate set and subsequently reducing this candidate set with reference to sequences of higher sensitivity;

reintegration—refers to the reinsertion out of excised bases or strings into an excised sequence, after alignment or another operation reveals a misclassification of the excised data by the filter;

correlation-free variant calling on excised information refers to the processing of genomic information data by reference to variants that are comprised of multiple-levels of sequences of multiple levels of sensitivity; and distributed sealed query processing relates to the addressing and processing of queries which temporarily require access to genomic information data of a level of sensitivity higher than the level which the query can access.

Referring to FIGS. 2 to 17 now, there are shown in diagrammatic form interdependencies of various features of embodiments of the present invention as introduced above, which will be more fully understood with reference to the description given herein.

As shown and illustrated herein, a fundamental principle of the invention is to construct a workflow for processing genomic information, wherein steps operate exclusively on genomic information with a lower-order of sensitivity relative to a sensitivity threshold, which is illustrated in FIG. 2 including the genomic information data obtained after individual steps. Bases, base pairs and strings thereof of a higher sensitivity are excised from genomic information data of a lower-sensitivity, and are protected by, through retention within, trusted storage and execution environments ("TEEs"). The genomic data processing tasks found in a classical genomic information pipeline, typically centralized, are performed by local or distributed algorithms, wherein algorithms processing higher-order sensitive data leverage the results of, and additional data produced by, algorithms processing lower-order sensitive or insensitive data.

Herein, two approaches to processing excised genomic information are distinguished. A first approach is to reintegrate excised bases or sequences into data sets of lower sensitivity for outputting temporary data sets of higher sensitivity, upon which operations are performed within TEE(s) corresponding to the highest level of sensitivity of the reintegrated genomic information, whereby the output genomic information of such further operations is then filtered and excised again before release to the process requestor. With this first approach, the standard sensitivity and excising-agnostic algorithms of classical genomic workflows can be used, provided that they fit the limited resources of TEEs which host these algorithms and that are cleared to the appropriate levels.

A second and main approach is to extract genomic information data at lower sensitivity levels, and ideally using only insensitive data, to reduce the processing resource requirements for carrying out operations at higher sensitivity level when they are carried out upon excised higher-sensitivity sequences: rather than re-executing the pipeline stages of the genomics workflow, existing output from processing lower-sensitivity level data is leveraged, by recombining these results with excised sequences. FIG. 3 illustrates this technique.

Details about how the above techniques are embodied in stages throughout the full genomic pipeline, and how the respective execution of steps may differ amongst alternative embodiments of the apparatus for secure genomic information processing, are described hereafter.

Embodiments of the genomic information processing pipeline with nested sensitivity levels disclosed herein and hereafter, are preferably implemented as one or more set(s) of data processing instructions for configuring a data processing apparatus, device and/or system that constitutes, or communicates with, at least one trusted execution environment. Several techniques have been proposed to create trusted execution environments ("TEEs") and to allow them to interoperate in a secure fashion. For example, Patent US 20160142396 proposes an infrastructure for secure communication between TEEs, an approach that has already been addressed before [Gro91] by connecting the authenticity (established through an authenticated boot) with a key required for communicating with the TEE. Patent US 20160182499 [pate] and U.S. Pat. No. 7,624,261 [patc] before it, both describe the secure incorporation of trusted peripheral devices into a system, by requiring their authentication prior to establishing communication with them.

The present invention is agnostic to the precise way in which secure communication with a TEE is established, how the code in this environment is authenticated to the remaining system, and how the TEE is constructed in the first place. As such the embodiments of the apparatus and methods can be based on a wide variety of different technologies, such as commercial off-the-shelf systems distributed by ARM® as Trustzone® or by Intel® as SGX®, or more dedicated systems that set aside processing resources to form the TEEs. Instead, the focus of computing embodiments of the methodology described herein, remains on the protection of sensitive sequences in genomic information and of the metadata that may identify an individual.

A generic embodiment of an apparatus according to the invention is shown in FIG. 4, which comprises at least one data collection system, composed of a sensor for reading genomic information; at least one data processing system, possibly comprised of multiple general purpose cores, GPGPUs, accelerators, FPGAs and the like, and configured to both post-process sensor data and execute the filtering and excising steps described herein; and at least one storage system for storing genomic information. The device may include a network of arbitrary kind and topology to connect these components.

All components may be located in the same machine, or in multiple machines connected through a local area network. In particular, all components and the storage are trusted to keep secure genomic information up to the highest sensitivity level. The processing system executes the pre-processing steps required to turn sensor data into sequences of bases and their confidence. Moreover, it provides resources for executing the filtering and excising steps and possibly further steps of the genomic workflow.

In an embodiment of the apparatus, with the exception of the sensor, the components are not trusted: instead, the apparatus further comprises at least one trusted-execution environment for executing genome information-related steps. A secure communication channel is established, either by the sensor or by one of several TEEs, to the other TEE(s) and encryption methods are used both to securely store genomic information in the storage system and to protect their integrity. This embodiment is agnostic in the exact nature of TEE used, provided that it guarantees the secure and authentic execution of the methods described herein.

Embodiments of the apparatus may comprise a multitude of trusted or untrusted sequencing machines (respectively illustrated by the two embodiments discussed immediately above), a multitude of data processing systems (without data collection system) and of a network of arbitrary kind and topology connecting these machines. In particular, the systems comprising this apparatus may be located at different sites and be under the jurisdiction of different owners and possibly even different legislations.

To simplify the following description, when a method is said to be executed in a TEE cleared to a given sensitivity level, this means a TEE in an untrusted sequencing machine or in an entirely trusted sequencing machine. In the latter case, all software and hardware components running on this machine are assumed trustworthy, to the extent of the sensitivity level of the genomic information which it processes. In the former case, only the TEEs have to be trustworthy to this extent.

The embodiment of the apparatus shown in FIG. 4 consists essentially of a computing device with a sensor for extracting genomic information from prepared samples of DNA, RNA, proteins or other sources. On the data-collection side, base-pair sequences (called reads) are extracted and a quality array attached thereto in a post-processing step. The methods described herein are agnostic to the actual sequencing method and to the length of reads, insofar as reads may contain only 30 bases or significantly more bases.

Two main machine embodiments are considered in preference. In the embodiment shown in FIG. 5, a sensor is connected to a trusted sequencing machine system configured with a filter according to the invention. The sensor post-processing, the interfacing and the filtering are executed in a computer system, which needs to be trusted to the highest sensitivity level at which genomic data can be trusted. The computer system can thus be comprised of a single machine (e.g. a laptop with a sensor embedded into a USB stick-like device), or of multiple machines provided that they all reside in the same trustworthy data collection environment.

Alternatively, in the embodiment shown in FIG. 6, an architecture is considered wherein, with the exception of the post-processing and the filtering, the balance of functionality is implemented and performed in untrusted components. The sensor then establishes a secure channel, typically through encryption mechanisms, into a trusted execution environment within which the filter executes, and wherein the insensitive information is released to a less-trusted environment only after the classification and excising is complete. All other parts remain encrypted with ciphers strong enough for their sensitivity level.

In the embodiment shown in FIG. 5, compute nodes, comprised of cores, GPUs, FPGAs and other accelerators and of different storage media, sample the sensor data, process it and pass it through the classifying filter and excising stages of the invention to obtain excised reads. In a first implementation, compute nodes are formed from a multi- or many-core system and are connected by on-chip networks with each other and with the sensor. In another implementation, compute nodes are distinct computer systems connected through a local area network of arbitrary kind and topology. The distinguishing feature of this first embodiment is that the entire system is trusted, and therefore must be installed within a mutually trustworthy environment and protected against both outsider and insider threats.

However, complications associated with this requisite degree of protection, suggest the second embodiment of FIG. 6. Instead of executing the user interface and other code that is required to coordinate the reading of genomic information, alongside algorithms that require access to privacy sensitive genomic information, the apparatus in this embodiment is assumed to provide trusted execution environments, for instance per Intel® SGX® "enclaves". Code which requires access to genomic information is then distinguished and executed inside the TEEs. Rather than exposing the raw sensor signal, from which privacy sensitive information could be derived, the sensor is required to pass its signals over a secrecy-preserving channel into the TEE within which this sensitive data is processed, filtered and excised. Throughout this process, genomic information is treated as if classified at the highest sensitivity level. After excision however, the data is released to TEEs of a corresponding level of sensitivity level and, possibly if the data is non-sensitive, to an untrusted environment.

Subsequent methods are agnostic to the exact nature of TEE(s) as provided by the apparatus. This however assumes attestation of the code which the TEE(s) execute (e.g. through a late code launch), and a means for protecting code, data integrity and confidentiality (e.g. by encrypting all TEE states or by setting aside partitions of the system that are inaccessible from the untrusted side).

The embodiments described with reference to FIGS. 4 to 6 all suggest local instances of an apparatus according to the invention. However, to scale the present solution according to any increasing workload, distributed installations with local systems owned by different companies, and possibly run in different countries with different legislation, are contemplated. A distributed approach to contributing systems may provide for distinct data-collection and data-processing systems, but it is also envisaged to distribute data-processing capacity only, for instance procured from a cloud computing platform provider. FIG. 7 illustrates such a system.

TEEs are assumed to come with one of the state-of-the-art methods for authenticating the code and configuration that has been booted in them, that they do have access to resources external to them (either directly or through a communication channel) and that they may therefore access external data and possibly multiplex their internal state by encrypting the content prior to externalization. Moreover, a standard infrastructure both for authenticating TEEs and for constructing channels through which they can communicate is assumed, for example as disclosed in [pata].

The methodology according to the invention firstly provides a technique for identifying sensitive substrings at multiple sensitivity levels in long reads. The subsequent steps of the genomic workflow are agnostic to the exact filtering method used: they merely assume short reads or substrings of long reads to be classified with a sensitivity level, which safely overestimates the sensitivity of the information that they contain. The filtering method detects and classifies sensitive sequences in long reads, i.e. those reads which contain more than 30 bases.

The density of sensitive sequences in human genomes requires substring classifiers to avoid classifying large parts of reads as sensitive. The following methods describe Bloom filter-based methods to identify sensitive substrings in raw genomic data.

Bloom filters are probabilistic data structures, which apply several hash functions for mapping a training set to multiple bits of a bit array, which are set to denote inclusion of the trained sample in the set of detected samples. Hashing inputs with the same functions and finding all bits set indicate a possible identification of the training set. However, because the hash functions are not free of collisions, other samples outside the training set may also be identified, falsely, as positive sets.

For long-read substring filtering, Bloom filters are applied to detect all sensitive sequences in raw genomic information, but possibly more. The present approach is to train Bloom filters for each sensitivity level, with a training set that identifies a given position as sensitive.

In a first embodiment of this filtering method, a Bloom filter is trained for each sensitivity level with sequences in which the $k^{th}$ letter is sensitive. These sequences of a given length n are obtained from the reference genome, by incorporating all known combinations of variations that are known to occur at the locations covered by the training sequence. The quantitative results of this filter reveal an increased training complexity and, hence, high false-positive rates together with an increased susceptibility to errors.

In a second embodiment, training is limited to combinations of m variations at most, within training sequences of size n. Values of m=8 and n=30 have been shown to result in a good balance when training with datasets from the 1000 genome project, however further insights and consideration of other samples may require different values for these parameters. Without sequencing errors, the detection performance of the second embodiment is near optimal. However, detection quality drops with increasing sequencing errors.

In a third embodiment, multiple Bloom filters are therefore trained for each sensitivity level, preferably at least two per sensitivity level, with sequences wherein the sensitive letter is at different locations (e.g. first and last), and wherein a letter of the read is considered as sensitive if either of these filters identify the letter as sensitive.

In all three embodiments, the sensitivity level of the letter is derived from the filter that detects it as sensitive. Partitioning of the training set ensures that Bloom filters of different levels are not trained with the same sequence. However, false positives attributable to the nature of the Bloom filter may still cause a sample to match in multiple such filters. The letter is pessimistically classified at the highest sensitivity level of the filters that positively detected this letter. Letters that are not identified by any filter are classified as insensitive. FIG. 8 illustrates this approach.

The methodology according to the invention further provides a technique for excising sensitive parts in raw genomic data, which splits the read before alignment into multiple data sets, wherein one data set contains only insensitive bases and other data sets contain bases identified to be sensitive plus a reference to their location of excision in the insensitive read. The technique can be applied to a same read with several sensitivity levels: in that case, sensitive data sets are further split into one data set per sensitivity level, wherein information of higher sensitivity is removed from data sets of lower sensitivity, and stored in a sensitivity level-respective data set.

Several embodiments are considered for this technique. In a first, simplistic embodiment, excised base(s) of higher sensitivity are unmarked within the data set from which they have been excised. In a second embodiment however, excised base(s) or sequences thereof with a higher sensitivity level relative to the balance of the read, are replaced by the character "N" within the lower-sensitivity read, wherein "N" is known to represent any nucleotide according to the FASTA and FASTQ file format. In a third embodiment, it is proposed to replace excised base(s) or sequences thereof with a higher sensitivity level relative to the balance of the read, with a new special character apt to indicate the location in the lower-sensitivity read from which the sensitive information was excised. This special character is preferably a character which is known to not be in use within the FASTA and FASTQ format, for instance "@". The methodology according to the invention considers an embodiment wherein any one of the excising techniques previously described is performed after alignment, and in particular the third embodiment described above is considered particularly suitable for short reads of 30 bases, wherein too few bases would likely remain after substring filtering, for an alignment based on insensitive sequences to be effective.

FIG. 9 illustrates how excising splits raw genomic information into multiple separately protected data sets immediately after the sensor and post processing algorithms of the sequencing machines have produced the reads, moreover after the filter of the invention has classified the letters of the read according to the sensitivity levels of the information which they may reveal. Excised base(s) or sequences thereof are removed from the sequences of lower sensitivity, and stored in separate data sets together with their location within the lower-sensitivity sequences. Excising is applied either after alignment, suitably when reads are short, or before alignment, suitably when reads exceed a size appropriately useful for whole-read classifiers.

Excising may be applied in a separate pass through the read after filtering stage. However, it can also be integrated directly into the filtering step as illustrated in FIG. 10. The integration is shown into a dual-level long read filter: while scanning and classifying the letters of the read, the letter under investigation is redirected into the output stream of the corresponding sensitivity level of the Bloom filter that has identified the letter as sensitive, or to the insensitive/non-sensitive output stream if none of the Bloom filters register it.

In that context, if the previous letter was insensitive, an excised character e.g. "@" is inserted into the previous stream. When a subsequent letter is found to belong to a lower sensitivity level, the streams of higher sensitivity are stored away. A new stream is created when the first sensitive letter at this level is identified.

Excising sensitive sequences from short reads makes these sequences unusable for subsequent processing steps. Too few bases are left for successfully aligning short reads with excised sensitive reads. Short reads are therefore not excised before alignment, but follow Cogo et al. by proposing the application of privacy-preserving alignment algorithms for reads detected as sensitive. Once aligned, the location of sensitive sequences is known. To secure the subsequent processing steps, an embodiment excises sensitive genomic data after alignment, i.e. applies an excising procedure previously described as the first, second or third embodiment of the excising step, to the aligned read.

For short reads, the filter only reveals whether the entire read is sensitive and, if so, at which level of sensitivity. Too few characters remain besides the sensitive ones to reliably locate the read in the reference genome. A reversion to standard secure alignment algorithms, such as homomorphic encryption [BEDM+12] to align the sensitive reads, is recommended. However, once the location of the read is known, the location of sensitive variants is also received. The less sensitive parts in the aligned genome can therefore be declassified to lower sensitivity levels. The subsequent variant-calling step can benefit from this split, by using standard fast plaintext variant-calling algorithms on the insensitive data sets, whilst recombining their results when incorporating sequences of higher sensitivity.

Excised information can be transmitted along with a revealed part in an encrypted form, so that the remaining parts of the workflow can be executed in a distributed fashion. Prior to excising, the whole genome needs to be secured for preventing any disclosure of privacy sensitive information.

All subsequent processing steps are designed to maintain the split of genomic information according to sequencing levels. For example, after variant-calling, excised variants are only accessible in the VCF files of their sensitivity level, but not in VCF files of lower sensitivity levels.

Reverting back to the processing pipeline, alignment is the task of reconstructing the genome by locating reads in the reference genome, respectively by identifying how reads of the same genome align to each other. A naive alignment moves the read over the reference genome and takes its quality values into account for computing the likelihood of a match. More performant alignment algorithms use pre-computed search trees [LD09, LTD+09] and seeds [AGM+90], i.e. a short but significant sub-sequence of the read, for reducing the set of possible matches.

Cogo et al. [CBCV15] suggest using different algorithms for aligning differently-classified reads. Insensitive reads can be aligned with standard algorithms such as Blast [AGM+90] or Bowtie [LTP+09] while more costly but privacy-preserving algorithms should be used for sensitive reads. Homomorphic encryption [BEDM+12, DCFT13, AKD03] and similar approaches [AL05, HEKM11, JKS08] operate directly on encrypted genomic information. Therefore, short of breaking the cipher, these operations can be executed in any environment as data is never revealed in plaintext. Compared to these approaches, the methods described herein are fully integrated into the genomic workflow and protect the genomic information after their alignment.

Patent CA 2852916A1 [patd] offloads genomic information processing, in particular alignment, into TEEs, which can be located in a cloud infrastructure. However, TEEs must protect critical applications against untrusted software in the same system and often also against adversaries with some level of physical access to the system. As such, they only offer a limited amount of fast resources, whereas accesses to the bulk of all system resources have to pass encryption units for guaranteeing data confidentiality and integrity. In contrast, the bulk processing workload is kept on insensitive sequences and outside TEEs, wherein methods and algorithms are executed inside TEEs for incorporating sensitive information into the results obtained from these insensitive-data processing steps. Applied to alignment, this means, a candidate set of possible locations on insensitive data is computed outside the TEE, which is then reduced by checking all locations in the candidate set according to whether they continue to match with the excised sensitive parts.

The methodology according to the invention thus also provides a technique for aligning excised reads to one or more reference genome(s), or to other reads. The method exploits state-of-the-art alignment algorithms for aligning the insensitive parts with variations described hereunder, according to the excising method used.

Short read alignment follows the standard algorithms for aligning insensitive reads and Cogo's approach for aligning sensitive reads, by applying a privacy-preserving alignment algorithm that is trustworthy for information at the reads' sensitivity level, so as to identifying possible locations in the genome. Following alignment, the reads are then excised as previously described, and communicated to subsequent processing steps.

For long reads with excised sequences of higher sensitivity, recombining alignment is proposed for identifying long read positions within the reference genome, respectively relative to other reads of the same genome, by recombining partial results from lower sensitivity levels with the excised information of higher sensitivity level that is available at this level, in TEEs. FIG. 11 illustrates this approach.

In a first step, standard alignment algorithms or variants thereof are applied on the insensitive data for obtaining a candidate set of possible locations of the read in the reference genome, respectively of reads relative to each other. A seed-based algorithm is shown with seed TCT extracted from the read. In the reference string shown, the seed can be located at positions 2, 8, 12 and at the end, denoted as position 42. However, consideration of the remaining insensitive part of the low sensitivity read (ATCT) already excludes position 2 and 8. For each possible overlap of the read with the reference genome, alignment computes an inexact match quality, e.g. a weighted editing distance, for obtaining the confidence of a match. Weights incorporate confidence in the correctness of the read and penalize insertions and deletions.

The present technique builds on top of these alignment algorithms, by adjusting the weight, modifying the standard methods to reveal all promising candidates, and refining a candidate set with the excised information at higher sensitivity levels.

That is, for each possible candidate location, e.g. 12 and 42 in the example, the higher sensitive recombining part, in a TEE with access to genomic information of higher sensitivity, computes the insertion point of the higher sensitive sequence relative to the candidate location, e.g. at offset 5 relative to the locations 12 and 42 in the example, then aligns the excised base or sequence relative to this location: if TCT matches at location 42 with leading ATCT at location 7, the sequence @ AAGCT@ A . . . A is searched starting from location 12 onwards. As with the insensitive part, sequencing errors, variants and excised sequences of still higher sensitivity make this match inexact.

The locations obtained reduce the candidate set, e.g. from {12, 42} to {42} in the example. However, because this reduced set incorporates information at higher sensitivity levels, which may allow adversaries to learn about the nature of the excised sequence, the reduced locations have to be classified and protected at the same sensitivity levels as the data which they include. This is because a read may not be aligned just from its insensitive parts that pinpoint an exact location when incorporating excised genomic information of higher sensitivity levels. Subsequent processing steps are complicated by this requirement to conceal reduced location sets from lower sensitivity levels to preserve the privacy of the genome-donating individuals and their relatives.

In case the respective locations of excised sensitive base(s) or sequences are not unanimously reflected in the lower sensitive read, e.g. wherein sensitive bases are simply removed from the sequence or replaced with the existing FASTA/FASTQ unknown character symbol "N", standard alignment algorithms are used to perform the alignment on insensitive sequences and portions thereof. The algorithms are modified to require all possible locations at which insensitive part aligns to be revealed. This approach is termed the initial set of candidate locations.

In case the respective locations of excised sensitive base(s) or sequences are recognizable from the lower sensitive read, e.g. wherein they are denoted by a special character such as "@", the alignment algorithm is modified as described above and, in addition, such that it will not penalize insertions at the location of "@" character(s), nor the removal of this character. In an alternative embodiment, seed-based algorithms can be modified to select the seed from a portion of the insensitive sequence that is not interrupted by "@".

In case of short reads, whole-read filters can be used wherein excising is deferred to the completion of the alignment step.

Given the initial set of candidate locations, the step of recombining alignment proceeds by matching the location candidates with sequences of higher sensitivity levels in TEEs, for discharging non-matching locations from this set.

Seed based algorithms, such as the embodiment shown in FIG. 11, benefit from not splitting the seed across excising points. An embodiment therefore considers to further modify seed-based algorithms, to exclude seeds that contain the excising character, e.g. "@", or the unknown symbol character "N".

The degree of pessimism applied to filtering for the purpose of mitigating the risk of missing privacy-sensitive sequences, and later genomic data processing techniques such as statistical analyses which need to collect sufficient results for declassifying a sensitive sequence, all require the reinsertion of excised sequences into data sets classified with a lower level of sensitivity, a technique termed 'reintegration'.

The reintegration method described herein fulfils this purpose, and starts by inserting the selected sequence at the excising point, e.g. replacing the characters "N" or "@" at their location in the excised sequence. However, because both the length and nature of sensitive sequences are concealed by these single characters, the location of insertion of those sequences that are excised after these characters, and the location of excised sequences in the reintegrated sequence, need to be updated for correctly identifying the insertion points.

With reference to FIG. 12, the declassification of sequences after alignment reveals whether a sequence was insensitive, or an excised sequence had a lower sensitivity level: the sequence now known to be less sensitive is reintegrated at the location from where it was excised, and all excised references to this sequence are updated to point to the new location. The same declassification is applied once sufficient evidence is gathered, that the read is determined to be no longer sensitive at its current level. Since sequences of any sequencing level that is larger than the sensitivity level of the destination sequence may follow, this offset updating method must be executed by TEEs of all corresponding levels.

Once variants and their locations are known, a next step is to attach metadata to those sequences, the role of which is already known. Examples of such metadata are unique identifiers used by the system to keep track of an individual's genomes and related files (e.g., the VCF files from variant-calling). In addition, metadata can also be attached without knowing the exact sequence that is responsible for this metadata. An example of this latter aspect includes annotating all genomes of patients that share a common rare disease.

Augmenting files with metadata is a standard procedure, but a challenge for excised genomic information processing is the linking with sensitive metadata which reveals sensitive sequences in the genome or which constitutes sensitive information in and of itself.

Standard methods for linking metadata can be applied to genomes with excised sensitive sequences. The only difference occurs in terms of controlling access to metadata that is linked to sensitive sequences. Metadata is assumed to be classified to at least the same level of sensitivity as the sensitive sequence to which it refers, or it may be classified at a higher level of sensitivity. Linked metadata is assumed to be similarly classified to the sequences to which it refers: if metadata reveals sensitive information about the patient, or if it indicates the presence of a sensitive base or substring, it is classified to at least at the same sensitivity level as this information, base or substring. Query processing, described hereinafter, preferably takes this classification into account.

The methodology according to the invention also provides a technique for executing variant-calling hierarchically on excised genomic information, where parts of the variants may be classified at different levels. The method ensures that flanking variants do not reveal the nature of other variants, even if initially classified at different sensitivity levels.

Variant-calling extracts all differences which distinguish one individual from another, by comparing the aligned genome against the reference genome and storing the differences into separate files, typically written according to the VCF file format, together with their location. This approach allows for more efficient processing in subsequent steps and reduces the size of the information that needs to be stored per individual.

Due to sequencing errors, a number of corrective measures are typically applied to prepare the data for variant-calling. Variant-calling has access to possibly-duplicated, and overlapping, aligned reads and extracts the difference relative to the reference into a VCF formatted file, i.e. it gives the sequences and locations of the difference, together with a confidence that the difference actually denotes a variation and not a read error.

However, variants may be accompanied by flanking variants, which may indicate the presence of sensitive bases. Therefore, in addition to the actual sensitive base or sequence, any flanking variant apt to indicate their presence needs to be excised for protecting the privacy of individuals.

In contrast to state-of-the-art methods for variant-calling, the compounded problem that relevant flanking variants may be classified at different sensitivity levels, with for instance variants of medium sensitivity flanking a base or sequence of still higher sensitivity, and that this information is split into different files at the excising step, need to be addressed.

In contrast to state-of-the-art variant-calling, the additional task and complexity stem from a classification of sub-sequences of reads which may be overly pessimistic and from the separate of datasets into different sensitivity levels and files as a result of excising. As with alignment, the aim is to leverage on the variant-calling results at lower sensitivity levels to refine these results with higher-sensitive sequences.

The first corrective step is duplicate marking, e.g. based on Picard. Marking complicates this task by hiding higher-sensitivity bases or sequences, before duplicate detection has identified them, wherein they may differ due to sequencing errors. Moreover, erroneous letters may be classified at different levels, either because of false positives in the filters, or because filters do not detect sequences that start or end with a sequencing error. The present approach is to mark sequences as similar solely based on the information at the current level of sensitivity, and to de-duplicate them when higher-sensitive sequences differ. The duplicate/no-duplicate metadata is kept at the respective levels, i.e. if a higher sensitivity sequence indicates a de-duplication of similar lower-level reads, this information will only be available at the higher level.

Similar effects show up in re-alignment pre-processing steps, when balancing insertions and deletions with SNPs and the like. They are pre-processed as in the case of a single sensitivity level, and results are kept at the level determined by the sensitivity of information included.

The separation of this information at multiple levels constitutes no problem for analysis steps after variant-calling, because these steps are in preparation for variant-calling only.

From this preparation, variant-calling compares the location of differences to the reference genome and a database of known variations at the given location to compute likelihoods for a variant to be present. The present hierarchical correlation-correcting variant-calling method for excised reads thereby starts analysing insensitive sequences without excising character. The so identified matches with the reference genome are discarded and the insensitive variants extracted into VCF files.

The remaining parts of the aligned reads form sub-sequences that cannot yet be identified with sufficient certainty or discarded as matching with the reference. For embodiments of the excising step with substituting characters, these sequences contain the unknown letter "N" or an excising site marker (e.g., "@"). An example of an insensitive variant is the sequence which indicates brown eye color when aligning against a blue eyed reference genome. The class of brown-eyed people is large enough to not reveal sensitive information by enclosing this sequence.

The present variant-calling methods proceeds with higher levels by temporarily reintegrating the sequences available at this level into the section that remain from insensitive variant-calling. The detected variant may thereby be higher classified than the sensitivity level of the variant. In this case, the sequence is reintegrated into the data set of this level as described in Section 6.4 and the variant extracted into the VCF file for variants at this level.

Due to the excising of higher sensitive substrings the alignment information at lower sensitivity levels may be imprecise. After detecting that all excised sequences, which initially prevented a further reduction of this set, have been declassified, the refined read locations can be declassified as well and the imprecision of the alignment reduced. For example, assume in the example of Section 6.3, the reference "@ AAGCT @ A . . . A" was falsely classified medium sensitive, but is actually low sensitive at location 42. Then, because this sequence reduced the candidate set from {12, 42} to {42}, it is safe to reveal the exact position of this read at the low sensitivity level.

FIG. 13 illustrates the variant-calling procedure. An important special case occurs when flanking variants indicate the existence of a more sensitive variant. For example, from such flanking variations, researchers were able to derive the presence of Prof. Watson's Alzheimer gene, which he deliberately removed before publishing his genome. Non correlating variant-calling prevents these attacks by classifying such flankings at the same high sensitivity level as the sequence they indicate and by declassifying them if this correlation could not be confirmed or if the correlated location is already classified at a lower level.

The later stages in the pipeline allow queries on processed and excised genomic information. Queries have a statistical nature, e.g. by testing the significance of occurrence of a certain sequence, or a more classical nature, e.g. correlating individuals with common indicators such as blue eyes and susceptible to a certain illness and then computing an aggregate over this correlation, as the ratio of individuals in this set relative to the set of individuals with blue eyes.

Several techniques are known to allow privacy-preserving queries on genomic information, including some which rely upon TEEs for ensuring privacy ([SAM+17], [patb], [ARH+ 14]). The present methodology differs from such prior art techniques, because it enables the automatic detection and excising of all known genomic variations and many other privacy-sensitive information from human genomes, such as disease-related genes. Furthermore, the usefulness of data is increased, by selectively enhancing the protection and control of privacy-sensitive portions of genomes, by maintaining that data and the processing of sensitive portions thereof within secured environments.

In processing queries, the present invention focuses upon leveraging information available at lower levels of sensitivity, which can be produced more efficiently by less trustworthy algorithms. The distributed processing of queries upscales such processing by leveraging sealed intermediate-result extraction with TEEs, possibly in different systems and possibly controlled by different entities, to that cooperate in a secure and privacy-preserving manner.

The methodology according to the invention thus provides a technique for sealing the intermediate results that are output when processing excised genomic information of a sensitivity level and/or another, wherein only TEEs with an access level equal to or exceeding the excised data's respective sensitivity level are cleared to access and process that information, and wherein such sealed intermediate results can be communicated between TEEs without revealing their content.

Given that premise, the methodology according to the invention also provides a technique for executing queries on excised genomic information, by decomposing and combining queries into subqueries, intermediate results of which may include genomic information with higher sensitivity. In particular, embodiments may distribute subqueries into TEEs cleared for processing genomic information data classified at higher sensitivity levels, and accordingly excised at the initial sequence post-processing stage, wherein such TEEs may thus access the excised data and process the subqueries therewith, and then excise and declassify the output subquery reply result produced in these TEEs once the higher-classified genomic information is no longer required.

After variants are extracted and metadata is attached, the genomic information is ready for statistical analyses and other queries issued by researchers for scientific purposes, by doctors for medical purposes and personalized medicine, or by authorised third parties such as law enforcement agencies for forensic analyses. The different requirements of these various roles, and relations between individuals with possibly conflicting opinions about how their genomic data should be used, complicate the processing of these queries. For example, an ancestor may impose a restriction on her genome for use in scientific studies, which must also apply to descendants, but this personal choice should not prevent descendants from receiving personalized medicine nor, given a relevant judicial authorisation, should law enforcement units should be able to run forensic tests irrespective of the permission of the individuals whose DNA is used in these tests.

In the present case, query processing is further complicated by the fact that sensitive information and metadata is classified and excised from lower sensitive data sets. In particular, complications arise when metadata is temporarily required to compute a query, result(s) of which may no longer reflects this metadata, or when temporary results do not meet the privacy threshold defined by a security policy, for instance because an insufficient number of data sets match the query.

As a premise to the distributed sealed intermediate-result extraction and processing technique, there first follows a description of an enforcement scheme, shown in FIG. 14, for controlling access decisions in the distributed genomic information processing system of the invention. Using a trusted device in possession, or under the of, the party that is trusted by an individual contributing their genomic information, a policy regulating the use of genomic information is defined and stored in a policy object in the TEE with the highest degree of sensitivity level of this device. As a feature specific to genomic information, this policy may include thresholds on the amount of data sets that must be contained in queries for preventing re-identification of individuals. Relatives of the individual may also define such policy objects. With the help of metadata information, which encodes the relationship between individuals, the TEE then extracts enforcement rules from the policy objects of related individuals. These rules anticipate the roles of users of this data and the sensitivity of the information stored therein.

Policy enforcement rules are distributed alongside the genomic information and traced by a policy enforcement subsystem executing in the TEEs of a processing subsystem, for allowing invalidation and updating of the enforcement rules if a policy should change. Policy enforcement rules influence query processing by authorizing which parts of the query are allowed to be processed on different data sets, and at which sensitivity level. Subqueries may therefore be authorized on insensitive data, or data with a lower degree of sensitivity, if the affected individuals authorize this type of query, or if they are collectively overruled by a judicial body for e.g. forensic purposes, and if they collect only information that is safe to be revealed at this level.

The advantage of the techniques disclosed herein, that is conferred to distributed query processing, applies when this is not the case, i.e. when a query produces intermediate results that still contain sensitive information, or when the intermediate result does not meet the threshold required to reveal this information at its current level or at the level of the user, for instance when declassification of intermediate results risks privacy violations.

As usual for processing queries in a distributed fashion, the system is assumed to decompose queries into smaller subqueries, collecting data from different locations, and possibly from different sensitivity levels, before feeding their respective results into subqueries which join or aggregate the intermediate results before declassifying the final result. To illustrate this decomposition, which is common to database management systems, let an example query seek for the ratio of people who share the sequence ATC at a given location and who have blue eyes. Due to the distributed storing capabilities of the systems disclosed herein, the genomes or metadata information indicating these characteristics, i.e. the location of the sequence ATC and/or blue eyes, may be distributed as well. Therefore, a typical split is to collect individuals with either of these features, followed by a join to select the intersection of the two results for removing double entries. In this example, the individual identifier, which is required for the join, may reveal sensitive information in correlation attacks. However, even if genomes and metadata of individuals are kept in a single place, only a few datasets may match these criteria, which may allow re-identification of individuals.

To counteract such potential attacks, the methodology proposes to reclassify queries, to seal their intermediate results, and then to declassify the final result only after privacy-violating intermediate data is excised. More precisely, when a query is received that either seeks to return genomic information with a higher sensitivity level, e.g. the individual identifier to positive matches, or returns a result which cannot be immediately classified, e.g. because too few datasets have been considered for the aggregate, the query is reclassified to a sensitivity level corresponding to the highest sensitivity level of the information required and involved by this query, in case of too few aggregates to a level reflecting the risk of re-identification. The results of this query are sealed to TEE(s) cleared for this higher level of sensitivity.

Sealing means that only TEEs at this level can access and process this excised genomic information, e.g. depending on the embodiment because it is encrypted whereby only TEEs at this level may decrypt the data successfully. Sealed query results can be extracted like normal results which do not violate privacy rules, and can be communicated to the TEE executing the aggregating subquery. As with data selecting queries, this aggregating query is reclassified to a higher sensitivity level for obtaining access to the sealed results. Higher sensitivity genomic information is then excised for meeting privacy thresholds in the process of computing the aggregate. The result of the aggregating query can then be declassified and returned to the user.

Accordingly, a technique for sealing may include negotiating a secure channel with the aggregating TEE and sending the query result to that aggregating TEE over this channel, encrypting the data in such a way that only the aggregating TEE can decrypt it, or encrypting the data with a key shared by all TEEs of a given sensitivity level. In the latter case, all TEEs of this level can decrypt the information, which decouples query scheduling from the sealing process. FIG. 15 illustrates the effect of sealing, FIG. 16 illustrates its application in distributed query processing and FIG. 17 illustrates the special case wherein a low-sensitivity query does not meet the privacy threshold until all results of subqueries are integrated.

In FIG. 16, after the user authenticates with a given role (a), it is able to submit queries under this role, which may be split into subqueries that are in turn classified depending on the sensitivity of information which they need (b). In general, subqueries are processed in a distributed manner (c). In case subqueries require access to more sensitive sequences or metadata, or if they fail to meet the privacy threshold for the results which they produce, they are reclassified (d) to a higher sensitivity level, and their results are sealed (e) prior to their submission to the aggregating subquery. To access this sealed information, the aggregating query also needs to be reclassified. The result of this query is downgraded (f), provided that high sensitive data is excised and provided that the excised aggregate meets the privacy threshold.

It will be appreciated that the embodiments of the present invention hereinbefore described are given by way of example only, and are not meant to be limiting of the invention in any way.

It will also be appreciated that features of the disclosed embodiments do not necessarily or essentially require to be used together in combination with one another, and that one or more features of the disclosed embodiments may advantageously be extracted from the embodiment and used in isolation within the scope of the invention, as defined in the statement of invention and/or the claims.

The invention claimed is:

1. A computing device, comprising:
   at least one data collection arrangement comprising at least one sensor for reading genomic information into at least one read of any length, the or each read comprising a sequence of bases;
   at least one data processing arrangement adapted to selectively filter each read with a plurality of classifying filters according to its length, wherein
   a first filter compares a short read with predetermined base(s) for determining whether genomic information in the read belongs to a given level of sensitivity, and
   a second filter compares parts of a long read with predetermined base(s) for determining whether genomic information in one or more of the parts belongs to the given level of sensitivity or another level of sensitivity,
   whereby one or more sensitive bases in the sequence are detected, the or each data processing arrangement being further adapted to excise each detected sensitive base from the or each filtered read, by replacing each detected sensitive base with a character, for outputting an insensitive sequence; and
   at least one data storage arrangement adapted to store said read genomic information.

2. A computing device according to claim 1, wherein the or each data collection arrangement, the or each processing arrangement, and the or each storage arrangement is/are:
   provided locally to one another and/or are provided within a single or common enclosure or on a common substrate or board, or
   provided separate or remotely from one another and/or are connected through or via a local area network.

3. A computing device according to claim 1, wherein one or more of the arrangements of the device implements a trusted execution environment for processing genomic information.

4. A computing device according to claim 3, wherein the at least one sensor is adapted to provide a secure communication channel to the trusted execution environment.

5. A computing device according to claim 1, adapted to read the genomic information into a long read exceeding 30 bases.

6. A method of processing genomic information comprising the steps of:
   reading genomic information from at least one data collection arrangement comprising at least one sensor, into at least one read of any length, the or each read comprising a sequence of bases;

executing a filtering process on each read selectively according to a length of the read with at least one data processing arrangement for detecting one or more sensitive bases in the sequence, wherein the filtering process comprises
  comparing a short read with predetermined base(s) in a first classifying filter for determining whether genomic information in the read belongs to a given level of sensitivity, or
  comparing parts of a long read with predetermined base(s) in a second classifying filter for determining whether genomic information in one or more of the parts belongs to the given level of sensitivity or another level of sensitivity;
executing an excising process on each filtered read with the at least one data processing arrangement for excising each detected sensitive base therefrom, by replacing each detected sensitive base with a character, and outputting an insensitive sequence; and
storing said read genomic information in at least one data storage arrangement.

7. A method according to claim 6, wherein the or each long read exceeds 30 bases.

8. A method according to claim 6, wherein the method comprises the further step of splitting the or each sequence into multiple data sets, wherein at least one data set contains each insensitive base, and at least one data sets contains each detected sensitive base and a reference to the location in the sequence of each excised base.

9. A method according to claim 6, wherein the step of executing the excising process splits the sequence into an insensitive level and at least one sensitive level.

10. A method according to claim 9, wherein the character is either a character "N", apt to represent any nucleotide according to the FASTA and FASTQ file format or a character "@", apt to indicate the location in the sequence at which the or each detected sensitive base is excised.

11. A method according to claim 6, comprising a further step of aligning each of the insensitive sequence to at least one reference genome or to other reads, wherein the step of excising is performed either before or after aligning as a function of the read length.

12. A method according to claim 11, comprising the further steps of
  comparing the or each aligned insensitive sequence against the or each reference genome or said other reads for detecting one or more differences ; and
  storing detected difference(s) and their respective location(s) into one or more data structures.

13. A method according to claim 11, comprising the further steps of
  comparing the or each aligned insensitive sequence against the or each reference genome or said other reads for detecting any base that both flanks a detected sensitive base in the aligned insensitive sequence and has a lower sensitivity level relative thereto, according to whether the flanking base is indicative of the presence of said detected sensitive base in the aligned read;
  wherein the step of executing an excising process is performed upon each detected flanking base.

14. A method according to claim 12,
comprising the further step of instantiating at least one trusted execution environment (TEE) with a respective level of access to sensitive data sets containing detected sensitive base(s); and
performing the step of comparing the or each aligned read within the instantiated TEE.

15. A method according to claim 8, comprising the further steps of
  instantiating at least one trusted execution environment (TEE) with a respective level of access to sensitive date sets containing detected sensitive base(s);
  receiving at least one data query for genomic information including at least one sensitive data set;
  classifying each query according to a comparison of the sensitivity of each sensitive data set against the access level of the TEE;
  processing the query whenever the access level of the TEE is equal to or exceeds the data set sensitivity; and
  outputting queried genomic information.

16. A method according to claim 15, comprising the further step of
  decomposing the or each received query into a plurality of subqueries; wherein
  the step of instantiating further comprises instantiating at least one aggregating trusted execution environment (TEE);
  the step of classifying further comprises classifying each subquery; and
  the step of processing further comprises processing each subquery and aggregating genomic information output from processed subqueries with the aggregating TEE.

17. A method according to claim 6, wherein
the step of instantiating further comprises negotiating at least one secure channel between at least two TEEs, the method comprising the further step of
  either encrypting genomic information data at a data-sending TEE, wherein only a data-receiving TEE may decrypt it;
  or encrypting genomic information data with a key shared by all TEEs of a same access level.

18. A method according to claim 6, wherein each base comprises a base pair.

19. A method according to claim 6, implemented by a genomic information sequencing machine or system.

20. A storage device for storing computer readable instructions which, when executed by at least one data processing device, causes the or each data processing device to:
  read genomic information from at least one sensor, into at least one read of any length, the or each read comprising a sequence of bases;
  execute a filtering process on each read selectively according to a length of the read for detecting one or more sensitive bases in the sequence, wherein the filtering process comprises
    comparing a short read with predetermined base(s) in a first classifying filter for determining whether genomic information in the read belongs to a given level of sensitivity, or
    comparing parts of a long read with predetermined base(s) in a second classifying filter for determining whether genomic information in one or more of the parts belongs to the given level of sensitivity or another level of sensitivity;
  execute an excising process on each filtered read, by replacing each sensitive base detected therein with a character, for outputting an insensitive sequence which omits each detected sensitive base; and
  store the genomic information read in at least one data storage arrangement.

* * * * *